(12) United States Patent
Nelson et al.

(10) Patent No.: US 10,688,164 B2
(45) Date of Patent: Jun. 23, 2020

(54) CMV VECTORS COMPRISING MICRORNA RECOGNITION ELEMENTS

(71) Applicant: OREGON HEALTH & SCIENCE UNIVERSITY, Portland, OR (US)

(72) Inventors: Jay Nelson, Lake Oswego, OR (US); Scott Hansen, Portland, OR (US); Meaghan H. Hancock, Aloha, OR (US); Louis Picker, Portland, OR (US); Klaus Frueh, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 15/356,627

(22) Filed: Nov. 20, 2016

(65) Prior Publication Data

US 2017/0143809 A1    May 25, 2017

Related U.S. Application Data

(60) Provisional application No. 62/365,259, filed on Jul. 21, 2016, provisional application No. 62/258,393, filed on Nov. 20, 2015.

(51) Int. Cl.
*A61K 39/00* (2006.01)
*C12N 15/86* (2006.01)
*A61K 39/12* (2006.01)

(52) U.S. Cl.
CPC .............. *A61K 39/00* (2013.01); *A61K 39/12* (2013.01); *C12N 15/86* (2013.01); *A61K 2039/5256* (2013.01); *A61K 2039/552* (2013.01); *A61K 2039/572* (2013.01); *C12N 2710/16134* (2013.01); *C12N 2710/16143* (2013.01); *C12N 2710/16162* (2013.01); *C12N 2740/15034* (2013.01)

(58) Field of Classification Search
CPC ... C12N 15/86; C12N 2310/141; A61K 39/00
See application file for complete search history.

(56) References Cited

U.S. PATENT DOCUMENTS

| | | | |
|---|---|---|---|
| 5,168,062 A | 12/1992 | Stinski | |
| 5,273,876 A | 12/1993 | Hock et al. | |
| 5,385,839 A | 1/1995 | Stinski | |
| 5,720,957 A | 2/1998 | Jones et al. | |
| 5,830,745 A | 11/1998 | Hock et al. | |
| 5,833,993 A | 11/1998 | Wardley et al. | |
| 6,033,671 A | 3/2000 | Frueh et al. | |
| 7,537,770 B2 | 5/2009 | Kemble et al. | |
| 7,611,718 B1 | 11/2009 | Kemble et al. | |
| 7,700,350 B2 | 4/2010 | Hahn | |
| 7,892,822 B1 | 2/2011 | Koszinowski et al. | |
| 9,249,427 B2 | 2/2016 | Picker et al. | |
| 9,541,553 B2 | 1/2017 | Picker et al. | |
| 9,783,823 B2 | 10/2017 | Picker et al. | |
| 9,862,972 B2 | 1/2018 | Picker et al. | |
| 9,982,241 B2 | 5/2018 | Picker et al. |
| 10,101,329 B2 | 10/2018 | Picker et al. |
| 10,167,321 B2 | 1/2019 | Carfi et al. |
| 2002/0176870 A1 | 11/2002 | Schall et al. |
| 2003/0118568 A1 | 6/2003 | Crew |
| 2003/0138454 A1 | 7/2003 | Hill et al. |
| 2004/0086489 A1 | 5/2004 | Schall et al. |
| 2004/0110188 A1 | 6/2004 | Hahn et al. |
| 2004/0248300 A1 | 12/2004 | Preston |
| 2005/0064394 A1 | 3/2005 | Liu et al. |
| 2005/0118192 A1 | 6/2005 | Boursnell et al. |
| 2006/0019369 A1 | 1/2006 | Hahn |
| 2008/0071037 A1 | 3/2008 | Carr et al. |
| 2008/0199493 A1 | 8/2008 | Picker et al. |
| 2009/0148435 A1 | 6/2009 | Lebreton et al. |
| 2009/0148447 A1 | 6/2009 | Ledbetter et al. |
| 2009/0148477 A1 | 6/2009 | Bruder et al. |
| 2009/0203144 A1 | 8/2009 | Beaton et al. |
| 2009/0297555 A1 | 12/2009 | Kemble et al. |
| 2010/0142823 A1 | 6/2010 | Wang et al. |
| 2013/0089559 A1 | 4/2013 | Grawunder et al. |
| 2013/0136768 A1 | 5/2013 | Picker et al. |
| 2013/0142823 A1 | 6/2013 | Picker et al. |
| 2013/0156808 A1 | 6/2013 | Jonjic |
| 2013/0202638 A1 | 8/2013 | Thirion et al. |
| 2014/0141038 A1 | 5/2014 | Picker et al. |
| 2016/0010112 A1 | 1/2016 | Picker et al. |
| 2016/0114027 A1 | 4/2016 | Hahn et al. |
| 2016/0354461 A1 | 12/2016 | Picker et al. |
| 2017/0350887 A1 | 12/2017 | Picker et al. |
| 2018/0016599 A1 | 1/2018 | Evans et al. |
| 2018/0087069 A1 | 3/2018 | Picker et al. |
| 2018/0133321 A1 | 5/2018 | Picker et al. |
| 2018/0282378 A1 | 10/2018 | Frueh et al. |
| 2018/0298404 A1 | 10/2018 | Frueh et al. |

FOREIGN PATENT DOCUMENTS

| EP | 0521427 A1 | 1/1993 |
|---|---|---|
| WO | WO-8810311 A1 | 12/1988 |

(Continued)

OTHER PUBLICATIONS

Hancock et al. Virology 425:133-142 (Year: 2012).*

(Continued)

*Primary Examiner* — Brian Whiteman
(74) *Attorney, Agent, or Firm* — Sterne, Kessler, Goldstein & Fox P.L.L.C.

(57) ABSTRACT

Disclosed herein are recombinant CMV vectors comprising heterologous antigens and microRNA recognition elements to silence expression of CMV genes in the presence of microRNA derived from myeloid cells, an active UL128 protein and an active UL130 protein. Also disclosed are recombinant CMV vectors comprising heterologous antigens and microRNA recognition elements to silence expression of CMV genes in the presence of microRNA derived from myeloid cells, an inactive UL128 protein and an inactive UL130 protein. Also disclosed are methods of generating an unconventional immune response using these vectors. Such an immune response is characterized by generation of a CD8+ T cell response that is predominantly restricted by MHC-II.

23 Claims, 12 Drawing Sheets

(56) References Cited

FOREIGN PATENT DOCUMENTS

| | | |
|---|---|---|
| WO | WO-9503399 A2 | 2/1995 |
| WO | WO-9604383 A1 | 2/1996 |
| WO | WO-9631241 A1 | 10/1996 |
| WO | WO-9906582 A1 | 2/1999 |
| WO | WO-9907869 A1 | 2/1999 |
| WO | WO-02062296 A2 | 8/2002 |
| WO | WO-2003093455 A2 | 11/2003 |
| WO | WO-2006031264 A2 | 3/2006 |
| WO | WO-2006125983 A1 | 11/2006 |
| WO | WO2010101663 A2 * | 9/2010 |
| WO | WO-2010101663 A2 | 9/2010 |
| WO | WO-2011093858 A1 | 8/2011 |
| WO | WO-2011119920 A2 | 9/2011 |
| WO | WO-2011138040 A2 | 11/2011 |
| WO | WO-2011143650 A2 | 11/2011 |
| WO | WO-2011143653 A2 | 11/2011 |
| WO | WO-2012170765 A2 | 12/2012 |
| WO | 2014138209 A1 | 9/2014 |
| WO | WO-2016011293 A1 | 1/2016 |
| WO | WO-2016130693 A1 | 8/2016 |
| WO | WO-2017087921 A1 | 5/2017 |
| WO | WO-2018005559 A1 | 1/2018 |

OTHER PUBLICATIONS

Gillicze et al. BioMed Research International pp. 1-9 (Year: 2014).*

Murrell et al. Journal of Virology 87: 10489-105000 (Year: 2013).*

Ryckman et al. Journal of Virology 82: 60-70 (Year: 2008).*

Kim et al., "Human Cytomegalovirus microRNA miR-US4-1 Inhibits CD8+ T Cell Responses by Targeting the Aminopeptidase ERAP1", Nature Immunology, 2011, vol. 12, No. 10, pp. 984-991.

Hansen, S.G., et al., "Effector memory T cell responses are associated with protection of rhesus monkeys form mucosal simian immunodeficiency virus challenge," Nat. Med 15(3):293-299, Nature Publishing Group, United Kingdom (2009).

Hansen, S.G., et al., "Profound early control of highly pathogenic SIV by an effector memory T-Cell vaccine," Nature 473(7348):523-527, Nature Publishing Group, United Kingdom (2011).

Hansen, S.G., et al., "Cytomegalovirus vectors violate CD8+ T cell epitope recognition paradigms," Science 340(6135): 1237874, American Association for the Advancement of Science, United States (2013).

Hansen, S.G., et al., "Immune Clearance of highly pathogenic SIV infection," Nature 502(7469):100-104, Nature Publishing Group, United Kingdom (2013).

Basta, S., et al., "Inhibitory Effects of Cytomegalovirus Proteins Us2 and Us11 Point to Contributions From Direct Priming and Cross-priming in Induction of Vaccinia Virus-specific Cd8(+) T Cells," Journal of Immunology 168(11):5403-5408, American Association of Immunologists, United States (Jun. 2002).

Besold, K., et al., "Immune Evasion Proteins GpUS2 and GpUS11 of Human Cytomegalovirus Incompletely Protect Infected Cells From CD8 T Cell Recognition," Virology 391(1):5-19, Academic Press, United States (Aug. 2009).

Borst, E and Messerle, M, "Development of a Cytomegalovirus Vector for Somatic Gene Therapy," Bone Marrow Transplant 25 Suppl 2:S80-S82, Nature Publishing Group (May 2000).

Borst, E.M and Messerle, M, "Construction of a Cytomegalovirus-based Amplicon: a Vector With a Unique Transfer Capacity," Human Gene Therapy 14(10):959-970, M.A. Liebert, United States (Jul. 2003).

Bresnahan, W.A and Shenk, T.E, "UL82 Virion Protein Activates Expression of Immediate Early Viral Genes in Human Cytomegalovirus-infected Cells," Proceedings of the National Academy of Sciences of the United States of America 97(26):14506-14511, National Academy of Sciences, United States (Dec. 2000).

Bresnahan, W.A., et al., "Replication of Wild-type and Mutant Human Cytomegalovirus in Life-extended Human Diploid Fibroblasts," Journal of Virology 74(22):10816-10818, American Society for Microbiology, United States (Nov. 2000).

Brondke, H. "Human Herpesvirus 5, Towne Strain," US3 (NCBI GenBank Ace. No. AAS49002), Dep. Apr. 8, 2004.

Brondke, H. "Human Herpesvirus 5, Towne Strain," US6 (NCBI GenBank Ace. No. AAS49004), Dep. Apr. 8, 2004.

Brown, B.D and Naldini.L, "Exploiting and Antagonizing MicroRNA Regulation for Therapeutic and Experimental Applications," Nature reviews Genetics 10(8):578-585, Nature Publishing Group, England (Aug. 2009).

Campadelli-Flume, et al., Editors, "Chapter 15: Betaherpes Viral Genes and Their Functions" Human Herpesviruses: Biology, Therapy, and Immunoprophylaxis. Cambridge: Cambridge University Press, 2007.

Cantrell, S.R and Bresnahan, W.A, "Human Cytomegalovirus (Hcmv) UL82 Gene Product (pp71) Relieves hDaxx-mediated Repression of Hcmv Replication," Journal of Virology 80(12):6188-6191, American Society for Microbiology, United States (Jun. 2006).

Cantrell, S.R and Bresnahan, W.A, "Interaction Between the Human Cytomegalovirus UL82 Gene Product (pp71) and HDaxx Regulates Immediate-early Gene Expression and Viral Replication," Journal of Virology 79(12):7792-7802, American Society for Microbiology, United States (Jun. 2005).

Chang, W.L and Barry, P.A, "Cloning of the Full-length Rhesus Cytomegalovirus Genome as an Infectious and Self-Excisable Bacterial Artificial Chromosome for Analysis of Viral Pathogenesis," Journal of Virology 77(9):5073-5083, American Society for Microbiology, United States (May 2003).

Chau, N.H., et al., "Transcriptional Regulation of the Human Cytomegalovirus Us11 Early Gene," Journal of Virology 73(2):863-870, American Society for Microbiology, United States (Feb. 1999).

Davison, A.J and Stow, N.D, "New Genes From Old: Redeployment of DUTPase by Herpesviruses," Journal of Virology 79(20):12880-12892, American Society for Microbiology, United States (Oct. 2005).

Dudek, T and Knipe, D.M, "Replication-defective Viruses as Vaccines and Vaccine Vectors," Virology 344(1):230-239, Academic Press, United States (Jan. 2006).

Dunn, W., et al., "Functional Profiling of a Human Cytomegalovirus Genome," Proceedings of the National Academy of Sciences of the United States of America 100(24):14223-14228, National Academy of Sciences, United States (Nov. 2003).

European Search Report for EP Application No. EP16200334,The Hague, dated May 18, 2017.

European Search Report for EP Application No. EP17197412, Munich, Germany, dated Apr. 23, 2018.

Pietra, G., et al., "The Emerging Role of HLA-E-restricted CD8+ T Lymphocytes in the Adaptive Immune Response to Pathogens and Tumors," Journal of Biomedicine and Biotechnology 2010(9070921):1-8, Hindawi, India (2010).

Goodrum, F., et al., "Human Cytomegalovirus Persistence," Cellular Microbiology 14(5):644-655, Wiley-Blackwell, England (May 2012).

Gorman, S., et al., "Prior Infection with Murine Cytomegalovirus (Mcmv) Limits the Immunocontraceptive Effects of an MCMV Vector Expressing the Mouse Zona-Pellucida-3 Protein," Vaccine 26(31):3860-3869, Elsevier Science, Netherlands (Jul. 2008).

Grimwood, J., et al. "NCBI GenBank Direct Submission," Ace. No. AC146906, Sub. Nov. 5, 2003.

Hagemier, S.C., "Functional Analysis of the Human Cytomegalovirus UL82 gene product PP71 protein during Virus Replication," Doctoral Dissertation, The University of Texas Southwestern Medical Center at Dallas, May 2007, pp. 1-181.

Hahn, G., et al., "Human Cytomegalovirus UL131-128 Genes are Indispensable for Virus Growth in Endothelial Cells and Virus Transfer to Leukocytes," Journal of Virology 78(18):10023-10033, American Society for Microbiology, United States (Sep. 2004).

Halary, F., et al., "Human Cytomegalovirus Binding to DC-SIGN is Required for Dendritic Cell Infection and Target Cell Trans-Infection," Immunity 17(5):653-664, Cell Press, United States (Nov. 2002 ).

(56) References Cited

OTHER PUBLICATIONS

Hansen, S.G., et al., "Complete Sequence and Genomic Analysis of Rhesus Cytomegalovirus," Journal of Virology 77(12):6620-6636, American Society for Microbiology, United States (Jun. 2003).

Hansen, S.G., et al., "Evasion of Cd8+ T Cells Is Critical for Superinfection by Cytomegalovirus," Science 328(5974):102-106, American Association for the Advancement of Science, United States (Apr. 2010).

International Search Report and Written opinion for International Application No. PCT/US2011/036657, Korean Intellectual Property Office, Republic of Korea, dated Mar. 28, 2012, 12 pages.

Jones, T.R., et al., "Multiple Independent Loci Within the Human Cytomegalovirus Unique Short Region Down-regulate Expression of Major Histocompatibility Complex Class I Heavy Chains," Journal of Virology 69(8):4830-4841, American Society for Microbiology, United States (Aug. 1995).

Jones, T.R., et al., "Replacement Mutagenesis of the Human Cytomegalovirus Genome: US10 and US11 Gene Products are Nonessential," Journal of Virology 65(11):5860-5872, American Society for Microbiology, United States (Nov. 1991).

Kaech, S.M., et al., "Effector and Memory T-cell Differentiation: Implications for Vaccine Development," Nature Reviews. Immunology 2(4):251-262, Nature Pub. Group, England (2002).

Kalejta, R.F, "Human Cytomegalovirus PP71: a New Viral Tool to Probe the Mechanisms of Cell Cycle Progression and Oncogenesis Controlled by the Retinoblastoma Family of Tumor Suppressors," Journal of Cellular Biochemistry 93(1):37-45, Wiley-Liss, United States (Sep. 2004).

Karrer, U., et al., "Expansion of Protective CD8+ T-Cell Responses Driven by Recombinant Cytomegaloviruses," Journal of Virology 78(5):2255-2264, American Society for Microbiology, United States (Mar. 2004).

Kropff, B and Mach, M, "Identification of the Gene Coding for Rhesus Cytomegalovirus Glycoprotein B and Immunological Analysis of the Protein," 78(Pt 8):1999-2007, Microbiology Society, England (Aug. 1997).

Lilja, A.E., et al., "Functional Genetic Analysis of Rhesus Cytomegalovirus: Rh01 Is an Epithelial Cell Tropism Factor," Journal of Virology 82(5):2170-2181, American Society for Microbiology, United States (Mar. 2008).

Mahmood, K., et al., "Human Cytomegalovirus Plasmid-based Amplicon Vector System for Gene Therapy," Genetic vaccines and therapy 3(1):1, BioMed Central, England (Jan. 2005).

Marshall, K.R., et al., "Activity and Intracellular Localization of the Human Cytomegalovirus Protein PP71," The Journal of general virology 83(Pt 7):1601-1612, Microbiology Society, England (Jul. 2002).

Maussang, D., et al., "Human Cytomegalovirus-encoded Chemokine Receptor US28 Promotes Tumorigenesis," Proceedings of the National Academy of Sciences of the United States of America 103(35):13068-13073, National Academy of Sciences, United States (Aug. 2006).

McGregor, A., et al., "Molecular, Biological, and in Vivo Characterization of the Guinea Pig Cytomegalovirus (CMV) Homologs of the Human CMV Matrix Proteins pp71 (UL82) and pp65 (UL83)," Journal of virology 78(18):9872-9889, American Society for Microbiology, United States (Sep. 2004).

Mohr, C.A., et al., "A Spread-deficient Cytomegalovirus for Assessment of First-target Cells in Vaccination," Journal of virology 84(15):7730-7742, American Society for Microbiology, United States (Aug. 2010 ).

Mohr, C.A., et al., "Engineering of Cytomegalovirus Genomes for Recombinant Live Herpesvirus Vaccines," International Journal of Medical Microbiology 298(1-2):115-125, Urban & Fischer Verlag, Germany (Jan. 2008).

Moutaftsi, M., et al., "Human Cytomegalovirus Inhibits Maturation and Impairs Function of Monocyte-derived Dendritic Cells," Blood 99(8):2913-2921, American Society of Hematology, United States (Apr. 2002).

Murphy, C.G., et al., "Vaccine Protection Against Simian Immunodeficiency Virus by Recombinant Strains of Herpes Simplex Virus," Journal of virology 74(17):7745-7754, American Society for Microbiology, United States (Sep. 2000).

Murphy, E., et al., "Coding Potential of Laboratory and Clinical Strains of Human Cytomegalovirus," Proceedings of the National Academy of Sciences of the United States of America 100(25):14976-14981, National Academy of Sciences, United States (Dec. 2003).

European Communication, dated Jun. 15, 2018, in Application No. 16200334.7, 6 pages.

Olaleye, O.D., et al., "Cytomegalovirus Infection Among Tuberculosis Patients in a Chest Hospital in Nigeria," Comparative Immunology, Microbiology and Infectious Diseases 13(2):101-106, Elsevier Science Ltd, England (1990).

Onuffer, J.J and Horuk, R, "Chemokines, Chemokine Receptors and Small-molecule Antagonists: Recent Developments," Trends in Pharmacological Sciences 23(10):459-467, Published by Elsevier in Association with the International Union of Pharmacology, England (Oct. 2002).

Oxford, K.L., et al., "Protein Coding Content of the ULb' Region of Wild-Type Rhesus Cytomegalovirus," Virology 373(1):181-188, Academic Press, United States (Mar. 2008).

Plotkin, S.A., et al., "Vaccines for the Prevention of Human Cytomegalovirus Infection," Reviews of Infectious Diseases 12 Suppl 7:S827-S838, University of Chicago Press, United States (Sep.-Oct. 1990).

Powers, C and Fruh, K, "Rhesus CMV: an Emerging Animal Model for Human CMV," Medical Microbiology and Immunology 197(2):109-115, Springer-Verlag, Germany (Jun. 2008).

Redwood, A.J., et al., "Use of a Murine Cytomegalovirus K181-derived Bacterial Artificial Chromosome as a Vaccine Vector for Immunocontraception," Journal of virology 79(5):2998-3008, American Society for Microbiology, United States (Mar. 2005).

Rizvanov, A.A., et al., "Generation of a Recombinant Cytomegalovirus for Expression of a Hantavirus Glycoprotein," Journal of virology 77(22):12203-12210, American Society for Microbiology, United States (Nov. 2003).

Ryckman, B.J., et al., "Characterization of the Human Cytomegalovirus Gh/gl/ul128-131 Complex That Mediates Entry Into Epithelial and Endothelial Cells," Journal of virology 82(1):60-70, American Society for Microbiology, United States (Jan. 2008).

Schleiss, M.R., et al., "Genetically Engineered Live-attenuated Cytomegalovirus (CMV) Vaccines Improve Pregnancy Outcome in the Guinea-pig Model of Congenital CMV Infection," Retrovirology 5(1):1-3, (Apr. 2008).

European Search Report for EP Application No. EP11008462, Munich, Germany, dated Jul. 26, 2012.

GenBank Report, Accession No. NP_057850, (published Aug. 1, 2000).

Geisler, A., et al., "MicroRNA-regulated viral vectors for gene therapy," World J Exp Med 6(2):37-54, Baishideng Publishing Group, United States (2016).

Oxxon Terapeutics Licenses Rights to Xenova's DISC-HSV and DISC-GM-CSF Vector Technolgies, BusinessWire, Jan. 13, 2005.

Tessmer, M.S., et al., "Salivary Gland NK Cells Are Phenotypically and Functionally Unique," PLoS Pathogens 7(1):e1001254, Public Library of Science, United States (Jan. 2011).

Ulmer, J.B, "Tuberculosis DNA Vaccines," Scandinavian Journal of Infectious Diseases 33(4):246-248, Informa Healthcare, England (2001).

Wiertz, E.J., et al., "The Human Cytomegalovirus US11 Gene Product Dislocates Mhc Class I Heavy Chains From the Endoplasmic Reticulum to the Cytosol," Cell 84(5):769-779, Cell Press, United States (Mar. 1996).

Altschul, S.F. and Gish W., "Local Alignment Statistics," Methods in Enzymology 266:460-480, Academic Press, United States (1996).

Altschul, S.F., et al., "Basic Local Alignment Search Tool," Journal of Molecular Biology 215(3):403-410, Elsevier, England (Oct. 1990).

Andre, S., et al., "Increased Immune Response Elicited by DNA Vaccination With a Synthetic gp120 Sequence With Optimized Codon Usage," Journal of Virology 72(2):1497-1503, American Society for Microbiology, United States (Feb. 1998).

(56) References Cited

OTHER PUBLICATIONS

Barsov, E.V., et al., "Transduction of Siv-specific Tcr Genes Into Rhesus Macaque Cd8+ T Cells Conveys the Ability to Suppress Siv Replication," PLoS One 6(8):e23703, Public Library of Science, United States ( Aug. 2011).

Do, J.S., et al., "Unexpected Role for MHC II-Peptide Complexes in Shaping CD8 T-Cell Expansion and Differentiation in Vivo," Proceedings of the National Academy of Sciences 109(31):12698-12703, National Academy of Sciences, United States (Jul. 2012).

Felgner, J.H., et al., "Enhanced Gene Delivery and Mechanism Studies With a Novel Series of Cationic Lipid Formulations," Journal of Biological Chemistry 269(4):2550-2561, American Society for Biochemistry and Molecular Biology, United States (Jan. 1994).

Gill, R.B., et al., "Coding Potential of Ul/b' From the Initial Source of Rhesus Cytomegalovirus Strain 68-1," Virology 447(1-2):208-212, Academic Press, United States (Dec. 2013).

Gish, W and States, D.J, "Identification of Protein Coding Regions by Database Similarity Search," Nature Genetics 3(3):266-272, Nature Publishing Group, United States (Mar. 1993).

Goodman-Snitkoff, G., et al., "Role of Intrastructural/ intermolecular Help in Immunization With Peptide-phospholipid Complexes," Journal of Immunology 147(2):410-415, American Association of Immunologists, United States (Jul. 1991).

Wang, D and Shenk,T ., "Human cytomegalovirus UL131 Open Reading Frame is Required for Epithelial Cell Tropism," Journal of Virology, 79(16):10330-10338, American Society for Microbiology, United States (Aug. 2005).

Hancock, M.H., et al., "Rhesus Cytomegalovirus Encodes Seventeen Micrornas that are Differentially Expressed In Vitro and In Vivo," Virology 425(2):133-142, Academic Press, United States (Apr. 2012).

Hansen, S.G., et al., "Broadly Targeted Cd8' T Cell Responses Restricted by Major Histocompatibility Complex E," Science 351(6274):714-720, American Association for the Advancement of Science, United States (Feb. 2016).

Higgins, D.G and Sharp, P.M, "CLUSTAL: A Package for Performing Multiple Sequence Alignment on a Microcomputer," Gene 73(1):237-244, Elsevier/North-Holland, Netherlands (Dec. 1988).

Higgins, D.G., and Sharp, P.M., "Fast and Sensitive Multiple Sequence Alignments on a Microcomputer," Computer Applications in the Biosciences 5(2):151-153, Oxford University Press, United Kingdom (Apr. 1989).

Huang, X., et al., "Parallelization of a Local Similarity Algorithm," Computer Applications in the Biosciences 8(2):155-165, Oxford University Press, England (Apr. 1992).

International Preliminary Report on Patentability for International Application No. PCT/US2016/017373, The International Bureau of WIPO, Geneva, Switzerland, dated Aug. 15, 2017, 8 pages.

International Search Report and Written Opinion for International Application No. PCT/US2015/040807, European Patent Office, HV Rijswijk, dated Oct. 28, 2015, 6 pages.

International Search Report and Written opinion for International Application No. PCT/US2016/017373, Korean Intellectual Property Office, Republic of Korea, dated May 23, 2016.

International Search Report for International Application No. PCT/US2012/041475, Korean Intellectual Property Office, Republic of Korea, dated Dec. 14, 2012.

James, SH and Prichard, M.N., "The Genetic Basis of Human Cytomegalovirus Resistance and Current Trends in Antiviral Resistance Analysis," Infectious Disorders Drug Targets, 11(5):504-513, Bentham Science Publishers, United Arab Emirates (Oct. 2011).

Karlin, S. and Altschul, S.E., "Methods for Assessing the Statistical Significance of Molecular Sequence Features by using General Scoring Schemes," Proceedings of the National Academy of Sciences USA 87(6):2264-2268, National Academy of Sciences, United States (Mar. 1990).

Karlin, S, and Altschul, S.F., "Applications and Statistics for Multiple High-scoring Segments in Molecular Sequences," Proceedings of the National Academy of Sciences USA 90(12):5873-5877, National Academy of Sciences, United States (Jun. 1993).

Malouli, D., et al., "Reevaluation of the Coding Potential and Proteomic Analysis of the Bac-derived Rhesus Cytomegalovirus Strain 68-1," Journal of Virology 86(17):8959-8973, American Society for Microbiology, United States (Sep. 2012).

McGregor, A., et al., "Expression of the Human Cytomegalovirus UL97 Gene in a Chimeric Guinea Pig Cytomegalovirus (GPCMV) Results in Viable Virus with Increased Susceptibility to Ganciclovir and Maribavir," Antiviral Research 78(3):250-259, Elsevier, Netherlands (Jun. 2008).

Miller, M.D., et al., "Vaccination of Rhesus Monkeys With Synthetic Peptide in a Fusogenic Proteoliposome Elicits Simian Immunodeficiency Virus-specific Cd8+ Cytotoxic T Lymphocytes," Journal of Experimental Medicine 176(6):1739-1744, Rockefeller University Press, United States (Dec. 1992).

Murrell, L., et al., "Impact of Sequence Variation in the UL128 Locus on Production of Human Cytomegalovirus in Fibroblast and Epithelial Cells," Journal of Virology 87(19):10489-10500, American Society for Microbiology, United States (Oct. 2013).

Myers, E.W., and Miller, W., "Optimal Alignment in Linear Space," Computer Applications in the Biosciences 4(1):1-13, Oxford University Press, England (Mar. 1988).

Needleman, S.B. and Wunsch, C.D., "A General Method Applicable to the Search for Similarities in the Amino Acid Sequence of Two Proteins," Journal of Molecular Biology 48(3):443-453, Academic Press, England (Mar. 1970).

Oxford, K.L., et al., "Protein Coding Content of the UL)b' Region of Wild-type Rhesus Cytomegalovirus," Virology, 373(1):181-183, Academic Press, United States (Mar. 2008).

Pearce, E.L., et al., "Functional Characterization of MHC Class II-Restricted CD8+CD4- and CD8-CD4-T cell Responses to Infection in CD4-/- Mice," Journal of Immunology 173(4):2494-2499, American Association of Immunologists, United States (Aug. 2004).

Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).

Pearson, W.R., "Using the FASTA Program to Search Protein and DNA Sequence Databases," Methods in Molecular Biology 24:307-331, Humana Press, United States (Feb. 1994).

Hanley, P.J., et al., "Controlling cytomegalovirus: helping the immune system take the lead,"Viruses, 6(6):2242-2258, MDPI, Switzerland (May 2014).

Heineman, T.C., "Chapter 71: Human cytomegalovirus vaccines." In: Arvin, A, Campadelli-Fiume, G, Mocarski, E, et al., eds. Human Herpesviruses: Biology, Therapy, and Immunoprophylaxis, Cambridge: Cambridge University Press, 2007.

Picker, L.J., et al., "New paradigms for HIV/AIDS vaccine development," Annual Review of Medicine 63:95-111, Annual Reviews, United States (Feb. 2012).

Pietra, G., et al., "HLA-E-Restricted Recognition of Cytomegalovirus-derived Peptides by Human CD8+ Cytolytic T Lymphocytes," Proceedings of the National Academy of Sciences of the United States of America 100(19):10896-10901, National Academy of Sciences, United States (Sep. 2003).

International Preliminary Report on Patentability for International Application No. PCT/US2015/040807 , The International Bureau of WIPO, Geneva, Switzerland, dated Jan. 17, 2017, 8 pages.

Joosten, S.A., et al., "Characteristics of HLA-E Restricted T-Cell Responses and Their Role in Infectious Diseases," Journal of Immunology Research, 2016:2695396, Hindawi Publishing Corporation, Egypt (Sep. 2016).

Lauron, E.J., et al., "Human Cytomegalovirus Infection of Langerhans-Type Dendritic Cells Does Not Require the Presence of the gH/gL/UL128-131A Complex and Is Blocked after Nuclear Deposition of Viral Genomes in Immature Cells, " Journal of Virology, 88(1): 403-416, American Society for Microbiology, United States (Jan. 2014).

Smith, I.L., et al., "High-level resistance of cytomegalovirus to ganciclovir is associated with alterations in both the UL97 and DNA polymerase genes," Journal of Infectious Diseases, 176(1): 69-77,

(56) References Cited

OTHER PUBLICATIONS

Oxford University Press, United States (Jul. 1997). Erratum in: Journal of Infectious Diseases, 177(4):1140-1141 (Apr. 1998).
Wu, F., et al., "Role of Specific MicroRNAs for Endothelial Function and Angiogenesis," Biochemical and Biophysical Research Communications 386(4):549-553, Elsevier, United States (Sep. 2009).
Sambrook, J., et al., "Molecular Cloning: A Laboratory Manual," Third Edition, Cold Spring Harbor Laboratory Press, United States (1989).
Schuessler, A., et al., "Charge Cluster-to-Alanine Scanning of UL 12B for Fine Tuning of the Endothelial Cell Tropism of Human Cytomegalovirus," Journal of Virology, 82(22):11239-11246, American Society for Microbiology, United States (Nov. 2008).
Schuessler, A., et al., "Mutational Mapping of UL130 of Human Cytomegalovirus Defines Peptide Motifs within the C-Terminal Third as Essential for Endothelial Cell Infection," Journal of Virology, 84(18): 9019-9026, American Society for Microbiology, United States (Sep. 2010).
Smith, T.F. and Waterman, M.S., "Comparison of Biosequences," Advances in Applied Mathematics 2(4):482-489, Academic Press, Inc., United States (Dec. 1981).
Michaelson, J.S and Leder, P., "RNAi Reveals Anti-Apoptotic and Transcriptionally Repressive Activities of DAXX," Journal of Cell Science 116(Pt 2):345-352, Company of Biologists, London (Jan. 2003).
Ulmer, J.B., et al., "Heterologous Protection against Influenza by injection of DNA Encoding a Viral Protein," Science 259(5102):1745-1749, American Association for the Advancement of Science, United States (Mar. 1993).
Cranage, M., et al., "Carriers for the delivery of a vaccine against respiratory syncytial virus," Expert Opinion on Biological therapy 5(7):939-952, Taylor & Francis, United States (2005).
Antonis, A.F., "Vaccination with recombinant modified vaccinia virus Ankara expressing bovine respiratory syncytial virus (bRSV) proteins protects calves against RSV challenge." Vaccine 15(25):4818-4827, Elsevier, Netherlands (2007).
Kovarik, J., et al., "Induction of adult-like antibody, Th1, and CTL responses to measles hemagglutinin by early life murine immunization with an attenuated vaccinia-derived NYVAC (K1L) viral vector," Virology 285(1):12-20, Elsevier, Netherlands (2001).
Welter, J., et al., "Mucosal vaccination with recombinant poxvirus vaccines protects ferrets against symptomatic CDV infection," Vaccine 17(4):308-318, Elsevier, Netherlands (1999).
Guillaume, V., et al., "Nipah Virus: Vaccination and passive protection studies in a hamster model," Journal of Virology 78(2):834-840, American Society for Microbiology, United States (2004).
Wyatt, L.S., et al., "Development of a replication-deficient recombinant vaccinia virus vaccine effective against parainfluenza virus 3 infection in an animal model," Vaccine 14(15):1451-1458, Elsevier, Netherlands (1996).
Kenjiro, I., et al., "Long-term protective immunity to rinderpest in cattle following a single vaccination with recombinant vaccinia virus expressing the virus haemagglutinin protein," Journal of General Virology 81(6):1439-1446.
Grey, F., et al., "A human cytomegalovirus-encoded microRNA regulates expression of multiple viral genes involved in replication," PLOS pathogens 3(11):1593-1602, Public Library of Science, United States (2007.).
Ojha, M., et al., "Spatial and cellular localization of calcium-dependent protease (CDP II) in *Allomyces arbuscula*," Journal of Cell Science 116:1095-1105, The Company of Biologists, United Kingdom (2003).
Powers, C.J., et al., "Signal peptide-Dependent Inhibition of MHC Class I Heavy Chain Translation by Rhesus Cytomegalovirus," PLOS Pathogens 4(10):e1000150, Public Library of Science, United States.
Powers, C., et al., "The US2-11 region of RhCMV is both necessary and sufficient to counteract CD8+ T-cell immunity during re-infection of rhesus macaques," 34th Annual International Herpesvirus Workshop, Jul. 25, 2009, Ithaca, New York.
Smith, M.S., et al., "Roles of Phosphatidylinositol 3-Kinase and NF-B in Human Cytomegalovirus-Mediated Monocyte Diapedesis and Adhesion: Strategy for Viral Persistence," Journal of Virology 81(14):7683-7694, American Society for Microbiology, United States (2007).
Bentz, G.L., et al., "Human Cytomegalovirus (HCMV) Infection of endothelial Cells Promotes Naïve Monocyte Extravasation and transfer of Productive Virus to Enhance Hematogenous Dissemination of HCMV," Journal of Virology 80(23):11539-15555, American Society for Microbiology, United States (2006).
Fruh, K., et al., "CD8+ T cell programming by cytomegalovirus vectors: applications in prophylactic and therapeutic vaccination," Current Opinion in Immunology 47:52-56, Elsevier, Netherlands(2017).
Prod'Homme, V., et al., "Human Cytomegalovirus UL40 Signal peptide Regulates Cell Surface Expression of the NK Cell Ligands HLA-E and gpUL18," J. Immunology 188(6):2794-2804, American Society of Immunologist, United States (2012).
Wu., H.L., et al., "Cytomegalovirus vaccine vector 68-1 elicits universal, MHC-E-restricted CD8 T-cell responses against SIV," Journal of Medical Primatology 44(5):313, Wiley Online Library, United States (2014).
Corpet, F, "Multiple Sequence Alignment With Hierarchical Clustering," Nucleic Acids Research 16(22):10881-10890, Oxford University Press, England (Nov. 1988).
Gerna, G., et al., "Dendritic-cell Infection by Human Cytomegalovirus Is Restricted to Strains Carrying Functional U1131-128 Genes and Mediates Efficient Viral Antigen Presentation to Cd8+ T Cells," Journal of General Virology 86(Pt 2)275-284, Microbiology Society, United Kingdom (Feb. 2005).
Bowman, J.J., et al., "Rhesus and Human Cytomegalovirus Glycoprotein L are Required for Infection and Cell-to-Cell Spread of Virus but Cannot Complement Each Other," Journal of Virology, 85(5):2089-2099, American Society for Microbiology, United States (Mar. 2011).
Hobom, U., et al., "Fast Screening Procedures for Random Transposon Libraries of Cloned Herpesvirus Genomes: Mutational Analysis of Human Cytomegalovirus Envelope Glycoprotein Genes," Journal of Virology, 74(17):7720-7729, American Society for Microbiology (Sep. 2000).
Snyder, C.M., et al., "Cross-presentation of a Spread-defective MCMV is Sufficient to Prime the Majority of Virus-specific CD8+T Cells," PLoS One, 5(3):e9681, Public Library of Science, United States (Mar. 2010).
Bego, M., et al., "Characterization of an Antisense Transcript Spanning the UI81-82 Locus of Human Cytomegalovirus," Journal of Virology, 79(17):11022-11034, American Society for Microbiology, United States (Sep. 2005).
Dhuruvasan, K., et al., "Roles of Host and Viral MicroRNAs in Human Cytomegalovirus Biology," Virus Research, 157(2):180-192, Elsevier Science, Netherlands (May 2011).
Dolan, A., et al., "Genetic Content of Wild-Type Human Cytomegalovirus," Journal of General Virology, 85(Pt 5):1301-1312, Microbiology Society, England (May 2004).
Final Office Action dated Mar. 14, 2016, in U.S. Appl. No. 14/179,152, inventors Picker, L., et al., filed Feb. 12, 2014, 16 pages.
Gilicze, A.B., et al., "Myeloid-Derived microRNAs, miR-223, miR27a, and miR-652, Are Dominant Players in Myeloid Regulation," BioMed Research International 2014:870267, Hindawi Publishing Corporation, United States (Aug. 2014).
Guo, X.Z., et al., "Rapid Cloning, Expression, and Functional Characterization of Paired αβ and γσ T-Cell Receptor Chains from Single-Cell Analysis," Molecular Therapy: Methods & Clinical Development, 3:15054, Cell Press, United States (Jan. 2016).
Hancock, J.M and Armstrong, J.S., "SIMPLE34: an Improved and Enhanced Implementation for Vax and Sun Computers of the Simple Algorithm for Analysis of Clustered Repetitive Motifs in Nucleotide Sequences," Computer Applications in the Biosciences,10(1):67-70, Oxford University Press, England (Feb. 1994).

(56) References Cited

OTHER PUBLICATIONS

Jarvis, M.A and Nelson, J.A., "Mechanisms of Human Cytomegalovirus Persistence and Latency," Frontiers in Bioscience 7:d1575-d1582, Frontiers in Bioscience Publications, United States (Jun. 2002).

Kenneson, A and Cannon, M.J., "Review and Meta-analysis of the Epidemiology of Congenital Cytomegalovirus (CMV) Infection," Reviews in Medical Virology 17(4):253-276, Wiley, England (Jul.-Aug. 2007).

Khan, N., et al., "Identification of Cytomegalovirus-Specific Cytotoxic T Lymphocytes in Vitro Is Greatly Enhanced by the Use of Recombinant Virus Lacking the Us2 to Us11 Region or Modified Vaccinia Virus Ankara Expressing Individual Viral Genes," Journal of Virology, 79(5):2869-2879, American Society for Microbiology, United States (Mar. 2005).

Matthews, T.J., et al., "Prospects for Development of a Vaccine against HTLV-III-related Disorders," AIDS Research and Human Retroviruses, 3(1):197-206, Mary Ann Liebert, United States (1987).

Nicholson J.P., et al., "Properties of Virion Transactivator Proteins encoded by Primate Cytomegaloviruses," Journal of Virology, 6:65, BioMed Central, England (May 2009).

Non final Office Action mailed U.S. Appl. No. 11/597,457 dated Aug. 4, 2015, in United States Patent Application No. 11/597,457, Picker, L.J. et al., filed Apr. 28, 2008.

Non-final Office Action dated Jan. 9, 2015, in U.S. Appl. No. 14/179,152, inventors Picker, L., et al., filed Feb. 12, 2014, 16 pages.

Noriega, V., et al., "Diverse Immune Evasion Strategies by Human Cytomegalovirus," Immunologic Research, 54(1-3):140-151, Humana Press, United States (Dec. 2012).

O'Connor, C.M., et al., "Host microRNA Regulation of Human Cytomegalovirus Immediate Early Protein Translation Promotes Viral Latency," Journal of Virology, 88(10):5524-5532, American Society for Microbiology, United States (May 2014).

Retrieved from the Internet: (URL: http://www.microma.org/microma/getTargets.do?matureName=hsa-miR-142-3p&organism=9606), last accessed Oct 6, 2015.

Supplementary European Search Report for EP Application No. EP 16749813, Munich, Germany, dated Aug. 29, 2018.

Wang, X., et al., "Murine Cytomegalovirus Abortively Infects Human Dendritic Cells, Leading to Expression and Presentation of Virally Vectored Genes," Journal of virology 77(13):7182-7192, American Society for Microbiology, United States (Jul. 2003).

\* cited by examiner

BAC DNA

Figure 10 miRNA-targeted tropism recombinants: Blocking viral growth in myeloid cells using miR-142-3p

CMV VECTORS COMPRISING MICRORNA RECOGNITION ELEMENTS

CROSS-REFERENCE TO RELATED APPLICATION

This application claims the priority benefit of the earlier filing date of U.S. Provisional Application No. 62/258,393, filed Nov. 20, 2015, entitled "CMV VECTORS COMPRISING MICRORNA RECOGNITION ELEMENTS," and U.S. Provisional Application No. 62/365,259, filed Jul. 21, 2016, entitled "CMV VECTORS COMPRISING MICRORNA RECOGNITION ELEMENTS," both of which are incorporated herein by reference in their entirety.

ACKNOWLEDGEMENT OF GOVERNMENT SUPPORT

This invention was created with the support of the United States government under the terms of grant number P01 AI094417, awarded by the National Institutes of Health. The United States government has certain rights in this invention.

TECHNICAL FIELD

Embodiments relate to the use of CMV vectors in immunization, and more specifically, the generation of modified versions of CMV vectors that elicit unconventional immune responses upon immunization with heterologous antigens.

BACKGROUND

Rhesus Cytomegalovirus vaccine vectors expressing Simian Immunodeficiency Virus proteins (RhCMV/SIV) provide protection from pathogenic SIV (Hansen S G et al., Nat Med 15, 293 (2009); Hansen S G et al., Nat 473, 523 (2011); both of which are incorporated by reference herein). This protection is fundamentally distinct from other T cell vaccines in its extreme efficacy and nearly instantaneous onset, with ~50% of vaccines manifesting complete control of viral replication following a profoundly blunted and contracted acute phase of viremia. Although RhCMV-protected macaques exhibited periodic low-level "blips" of viremia, CD4+ memory T cell depletion was not observed, SIV-specific antibody responses did not develop, and subsequently, over time, viral nucleic acid became barely quantifiable while replication competent virus disappeared from the tissues of protected animals. These events did not occur in spontaneous SIV elite controllers and DNA prime/Ad5 boost vaccinated controllers (Hansen S G et al., Nature 502, 100 (2013); incorporated by reference herein). Given the central role of RhCMV-induced CD8+ T cells in mediating this protective effect in RhCMV/SIV-vaccinated macaques, defining the functional properties of these T cells is critical to understanding their mechanistic contribution to RhCMV/SIV vector-induced control of SIV replication. Understanding these properties may in turn lead to new uses for cytomegalovirus vaccine vectors expressing heterologous antigens.

CMVs may establish latency and reactivate in cells of the myeloid lineage, and macrophages play a central role in viral dissemination. In addition, dendritic cells are essential antigen presenting cell in vivo. CMV vectors that express heterologous antigens specifically constructed that they fail to replicate in such cells may be used as new vaccine candidates eliciting a modified, unconventional immune profile.

SUMMARY

Disclosed herein are cytomegalovirus (CMV) vectors comprising a first nucleic acid sequence that encodes at least one heterologous antigen; and a second nucleic acid sequence comprising a microRNA recognition element (MRE) that silences expression in the presence of a microRNA that is expressed by a cell of the myeloid lineage. The microRNA recognition element is operably linked to a CMV gene that is essential or augmenting for CMV growth in vivo. The vector also includes a nucleic acid sequence encoding an active UL128 protein (or ortholog thereof) and a nucleic acid sequence encoding an active UL130 protein (or ortholog thereof). In some embodiments, the vector will lack an active UL128 protein and an active UL130 protein.

Also disclosed herein are methods of generating an immune response to at least one heterologous antigen in a subject. The method involves administering to the subject a CMV vector of the type disclosed herein in an amount effective to elicit a CD8+ T cell response to the heterologous antigen. The immune response may be characterized by at least 10% of the CD8+ T cells being restricted by Class II MHC and by fewer than 10% of the cells being restricted by MHC-E.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 3A is an image of a gel showing the results where PCR using primers flanking the insertion sites demonstrate the insertion of the galK expression cassette and its replacement with the miR-142 3p target sites; in accordance with various embodiments;

FIG. 3B is an image of a gel showing XmaI digestion of BAC DNA indicating maintenance of an intact genome; in accordance with various embodiments;

FIG. 3C is an image of a gel showing BAC genomic DNA was isolated and electroporated into rhesus fibroblasts. Virus was plaque-purified, and viral DNA isolated at each of three passages and analyzed by PCR for maintenance of the miR-142 3p target site insertions. In addition, these PCR products were sequenced, and no mutations were detected, in accordance with various embodiments;

FIG. 3D is an image of a gel showing gag and HA expression from the construct, in accordance with various embodiments;

FIG. 10 is a schematic of the generation of RhCMV Rh156/Rh108 miR-142 3p mutant virus via galK recombination, in accordance with various embodiments;

FIG. 11A is an image of a gel showing the results wherein PCR using primers flanking the insertion sites demonstrate the insertion of the galK expression cassette and its replacement with the miR-142 3p target sites. In addition, BAC genomic DNA was isolated and electroporated into rhesus fibroblasts. Virus was plaque-purified and viral DNA isolated at each of three passages (P1, P2 and P3) and analyzed by PCR for maintenance of the miR-142 3p target site insertions. These PCR products were sequenced and no mutations were detected, in accordance with various embodiments;

FIG. 11B is an image of a gel showing Xmal digestion of RhCMV 68-1.2 GAG Rh156/Rh108 miR-142 3p BAC DNA indicating maintenance of an intact genome, in accordance with various embodiments;

FIG. 11C is an image of a gel showing GAG expression throughout 3 passages of RhCMV 68-1.2 GAG Rh156/Rh108 miR-142 3p in rhesus fibroblasts, in accordance with various embodiments;

DETAILED DESCRIPTION OF DISCLOSED EMBODIMENTS

Figure 1:
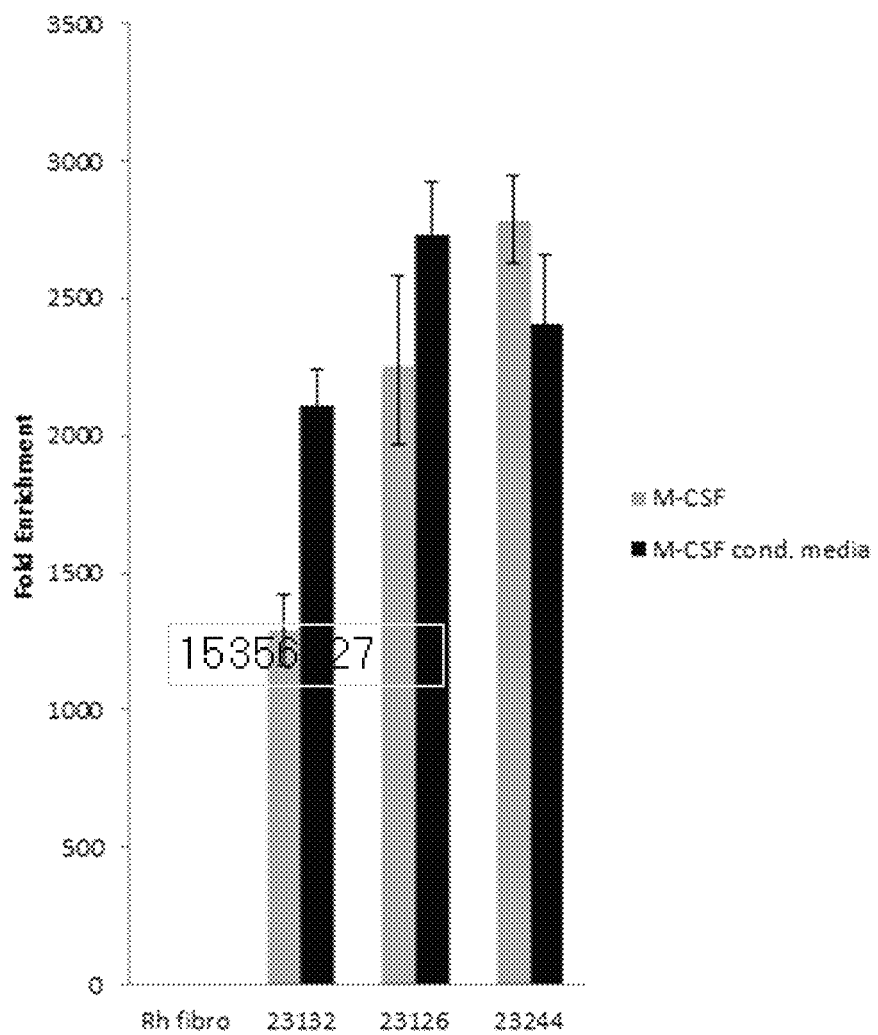
FIG. 1 is a bar graph showing miR-142-3p expression in CD14+ PBMCs from rhesus macaques differentiated using M-CSF or M-CSF conditioned media, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide novel, recombinant CMV vectors including but not limited to recombinant CMV vectors comprising a nucleic acid encoding at least one heterologous protein antigen, and at least one microRNA recognition element specific for a microRNA expressed by a cell of myeloid lineage that is operably linked to a CMV gene that is essential or augmenting for growth in vivo. Methods of using the novel, recombinant CMV vectors, such as methods of generating an immune response to the heterologous antigen in the subject are further disclosed.

I. Terms

Unless otherwise noted, technical terms are used according to conventional usage. All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference. Although methods and materials similar or equivalent to those described herein may be used in the practice or testing of this disclosure, suitable methods and materials are described below. In addition, the materials, methods, and examples are illustrative only and not intended to be limiting. In order to facilitate review of the various embodiments of the disclosure, the following explanations of specific terms are provided:

Antigen: As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

Administration: As used herein, the term "administration" means to provide or give a subject an agent, such as a composition comprising an effective amount of a CMV vector comprising an exogenous antigen by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Effective amount: As used herein, the term "effective amount" refers to an amount of an agent, such as a CMV vector comprising a heterologous antigen or a transfected CD8+ T cell, that recognizes a MHC-E/heterologous antigen-derived peptide complex, that is sufficient to generate a desired response, such as reduce or eliminate a sign or symptom of a condition or disease or induce an immune response to an antigen. In some examples, an "effective amount" is one that treats (including prophylaxis) one or more symptoms and/or underlying causes of any of a disorder or disease. An effective amount may be a therapeutically effective amount, including an amount that prevents one or more signs or symptoms of a particular disease or condition from developing, such as one or more signs or symptoms associated with infectious disease, cancer, or autoimmune disease.

MicroRNA: As used herein, the term "microRNA" refers to a major class of biomolecules involved in control of gene expression. For example, in human heart, liver or brain, miRNAs play a role in tissue specification or cell lineage decisions. In addition, miRNAs influence a variety of processes, including early development, cell proliferation and cell death, and apoptosis and fat metabolism. The large number of miRNA genes, the diverse expression patterns, and the abundance of potential miRNA targets suggest that miRNAs may be a significant source of genetic diversity.

A mature miRNA is typically an 18-25 nucleotide noncoding RNA that regulates expression of an mRNA including sequences complementary to the miRNA. These small RNA molecules are known to control gene expression by regulating the stability and/or translation of mRNAs. For example, miRNAs bind to the 3' UTR of target mRNAs and suppress translation. MiRNAs may also bind to target mRNAs and mediate gene silencing through the RNAi pathway. MiRNAs may also regulate gene expression by causing chromatin condensation.

A miRNA silences translation of one or more specific mRNA molecules by binding to a miRNA recognition element (MRE,) which is defined as any sequence that directly base pairs with and interacts with the miRNA somewhere on the mRNA transcript. Often, the MRE is present in the 3' untranslated region (UTR) of the mRNA, but it may also be present in the coding sequence or in the 5' UTR. MREs are not necessarily perfect complements to miRNAs, usually having only a few bases of complementarity to the miRNA and often containing one or more mismatches within those bases of complimentarity. The MRE may be any sequence capable of being bound by a miRNA sufficiently that the translation of a gene to which the MRE is operably linked (such as a CMV gene that is essential or augmenting for growth in vivo) is repressed by a miRNA silencing mechanism such as the RISC.

Mutation: As used herein, the term "mutation" refers to any difference in a nucleic acid or polypeptide sequence from a normal, consensus, or "wild type" sequence. A mutant is any protein or nucleic acid sequence comprising a mutation. In addition, a cell or an organism with a mutation may also be referred to as a mutant.

Some types of coding sequence mutations include point mutations (differences in individual nucleotides or amino acids); silent mutations (differences in nucleotides that do not result in an amino acid changes); deletions (differences in which one or more nucleotides or amino acids are missing, up to and including a deletion of the entire coding sequence of a gene); frameshift mutations (differences in which deletion of a number of nucleotides indivisible by 3 results in an alteration of the amino acid sequence. A mutation that results in a difference in an amino acid may also be called an amino acid substitution mutation. Amino acid substitution mutations may be described by the amino acid change relative to wild type at a particular position in the amino acid sequence.

Nucleotide sequences or nucleic acid sequences: As used herein, the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double stranded (duplex). Duplex nucleic acids may be homoduplex or heteroduplex.

Operably Linked: As the term "operably linked" is used herein, a first nucleic acid sequence is operably linked with a second nucleic acid sequence when the first nucleic acid sequence is placed in such a way that it has an effect upon the second nucleic acid sequence. For instance, a MRE is operably linked to a coding sequence that it silences if binding of the miRNA to the MRE silences the expression of the coding sequence. Operably linked DNA sequences may be contiguous, or they may operate at a distance.

Promoter: As used herein, the term "promoter" may refer to any of a number of nucleic acid control sequences that directs transcription of a nucleic acid. Typically, a eukaryotic promoter includes necessary nucleic acid sequences near the start site of transcription, such as, in the case of a polymerase II type promoter, a TATA element or any other specific DNA sequence that is recognized by one or more transcription factors. Expression by a promoter may be further modulated by enhancer or repressor elements. Numerous examples of promoters are available and well known to those of ordinary skill in the art. A nucleic acid comprising a promoter operably linked to a nucleic acid sequence that codes for a particular polypeptide may be termed an expression vector.

Recombinant: As used herein, the term "recombinant" with reference to a nucleic acid or polypeptide refers to one that has a sequence that is not naturally occurring or has a sequence that is made by an artificial combination of two or more otherwise separated segments of sequence, for example a CMV vector comprising a heterologous antigen and/or made replication deficient by the addition of a miRNA response element operably linked to a CMV gene that is essential or augmenting for growth in vivo. This artificial combination is often accomplished by chemical synthesis or, more commonly, by the artificial manipulation of isolated segments of nucleic acids, e.g., by genetic engineering techniques. A recombinant polypeptide may also refer to a polypeptide that has been made using recombinant nucleic acids, including recombinant nucleic acids transferred to a host organism that is not the natural source of the polypeptide (for example, nucleic acids encoding polypeptides that form a CMV vector comprising a heterologous antigen).

Replication-deficient: As used herein, a "replication deficient" CMV is a virus that once in a host cell, cannot undergo viral replication, or is significantly limited in its ability to replicate its genome and thus produce virions. In other examples, replication-deficient viruses may be dissemination-deficient, e.g., they are capable of replicating their genomes, but unable to infect another cell either because virus particles are not released from the infected cell or because non-infectious viral particles are released. In other examples, replication-deficient viruses are spread-deficient, e.g. infectious virus is not secreted from the infected host are therefore the virus is unable to spread from host to host. In some embodiments, a replication-deficient CMV is a CMV comprising a mutation that results in a lack of expression of one or more genes essential for viral replication ("essential genes") or required for optimal replication ("augmenting genes"). CMV essential and augmenting genes have been described in the art (in particular US 2013/0136768, which is incorporated by reference herein) and are disclosed herein.

Pharmaceutically acceptable carriers: As used herein, a "pharmaceutically acceptable carrier" of use is conventional. *Remington's Pharmaceutical Sciences*, by E. W. Martin, Mack Publishing Co., Easton, Pa., 19th Edition, 1995, describes compositions and formulations suitable for pharmaceutical delivery of the compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (such as powder, pill, tablet, or capsule forms), conventional non-toxic solid carriers may include, for example, pharmaceutical grades of mannitol, lactose, starch, or magnesium stearate. In addition to biologically neutral carriers, pharmaceutical compositions to be administered may contain minor amounts of non-toxic auxiliary substances, such as wetting or emulsifying agents, preservatives, and pH buffering agents and the like, for example sodium acetate or sorbitan monolaurate.

Polynucleotide: As used herein, the term "polynucleotide" refers to a polymer of ribonucleic acid (RNA) or deoxyribonucleic acid (DNA). A polynucleotide is made up of four bases: adenine, cytosine, guanine, and thymine/uracil (uracil is used in RNA). A coding sequence from a nucleic acid is indicative of the sequence of the protein encoded by the nucleic acid.

Polypeptide: The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

Sequence identity/similarity: As used herein, the identity/similarity between two or more nucleic acid sequences, or two or more amino acid sequences, is expressed in terms of the identity or similarity between the sequences. Sequence identity may be measured in terms of percentage identity; the higher the percentage, the more identical the sequences are. Sequence similarity may be measured in terms of percentage identity or similarity (which takes into account conservative amino acid substitutions); the higher the percentage, the more similar the sequences are. Polypeptides or protein domains thereof that have a significant amount of sequence identity and also function the same or similarly to one another (for example, proteins that serve the same functions in different species or mutant forms of a protein that do not change the function of the protein or the magnitude thereof) may be called "homologs."

Methods of alignment of sequences for comparison are well known in the art. Various programs and alignment algorithms are described in: Smith & Waterman, *Adv. Appl. Math* 2, 482 (1981); Needleman & Wunsch, *J Mol Biol* 48, 443 (1970); Pearson & Lipman, *Proc Natl Acad Sci USA* 85, 2444 (1988); Higgins & Sharp, *Gene* 73, 237-244 (1988); Higgins & Sharp, *CABIOS* 5, 151-153 (1989); Corpet et al, *Nuc Acids Res* 16, 10881-10890 (1988); Huang et al, *Computer App Biosci* 8, 155-165 (1992); and Pearson et al, *Meth Mol Bio* 24, 307-331 (1994). In addition, Altschul et al, *J Mol Biol* 215, 403-410 (1990), presents a detailed consideration of sequence alignment methods and homology calculations.

The NCBI Basic Local Alignment Search Tool (BLAST) (Altschul et al, (1990) supra) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information may be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr database, swissprot database, and patented sequences database. Queries searched with the blastn program are filtered with DUST (Hancock & Armstrong, *Comput Appl Biosci* 10, 67-70 (1994.) Other programs use SEG. In addition, a manual alignment may be performed. Proteins with even greater similarity will show increasing percentage identities when assessed by this method, such as at least about 75%, 80%, 85%, 90%, 95%, 98%, or 99% sequence identity to a protein.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and may possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence may be made using this degeneracy to produce multiple nucleic acid molecules that all encode substantially the same protein. Such homologous nucleic acid sequences may, for example, possess at least about 50%, 60%, 70%, 80%, 90%, 95%, 98%, or 99% sequence identity to a nucleic acid that encodes a protein.

Subject: As used herein, the term "subject" refers to a living multi-cellular vertebrate organisms, a category that includes both human and non-human mammals.

Treatment: As used herein, the term "treatment" refers to an intervention that ameliorates a sign or symptom of a disease or pathological condition. As used herein, the terms "treatment", "treat" and "treating," with reference to a disease, pathological condition or symptom, also refer to any observable beneficial effect of the treatment. The beneficial effect may be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

II. Recombinant CMV Vectors and Methods of Using the Same

Disclosed herein are human or animal CMV vectors capable of repeatedly infecting an organism. The CMV vectors comprise a nucleic acid sequence that encodes a heterologous protein antigen and further comprise a nucleic acid sequence that serves as a miRNA response element (MRE) that silences expression in the presence of a miRNA expressed by myeloid cells. Examples of such miRNAs expressed by myeloid cells include miR-142-3p, miR-223, miR-27a, miR-652, miR-155, miR-146a, miR-132, miR-21, and/or miR-125 (Gilicze A B et al, *Biomed Res Int* 2014, 870267 (2014); incorporated by reference herein) The MRE is operably linked to a CMV gene that is essential or augmenting for CMV growth in vivo. Examples of such genes include I-E2, and UL79, or orthologs thereof. One, two, three or more CMV genes may each be operably linked to one, two, three or more MREs in the vector. The vector also encodes an active UL128 gene and an active UL130 gene. Alternatively, the vectors may lack an active UL128 and an active UL130 gene.

The MRE may be any miRNA recognition element that silences expression in the presence of a miRNA expressed by myeloid cells. Such an MRE may be the exact complement of a miRNA. Alternatively, other sequences may be used as MREs for a given miRNA. For example, MREs may be predicted from sequences. In one example, the miRNA may be searched on the microRNA.org website. In turn, a list of mRNA targets of the miRNA will be listed. For example, the microRNA.org website for hsa-miR-142-3p will list putative mRNA targets of miR-142-3p. For each listed target on the page, 'alignment details' may be accessed and putative MREs accessed.

One of ordinary skill in the art may select a validated, putative, or mutated MRE sequence from the literature that would be predicted to induce silencing in the presence of a miRNA expressed in a myeloid cell such as a macrophage. One example involves the above referenced website. The person of ordinary skill in the art may then obtain an expression construct whereby a reporter gene (such as a fluorescent protein, enzyme, or other reporter gene) has expression driven by a promoter such as a constitutively active promoter or cell specific promoter. The MRE sequence may then be introduced into the expression construct. The expression construct may be transfected into an appropriate cell, and the cell transfected with the miRNA of interest. A lack of expression of the reporter gene indicates that the MRE silences gene expression in the presence of the miRNA.

The heterologous antigen may be any antigen, including a pathogen specific antigen derived from, for example, human immunodeficiency virus, simian immunodeficiency virus, herpes simplex virus type 1, herpes simplex virus type 2, hepatitis B virus, hepatitis C virus, papillomavirus, *Plasmodium* parasites, *Clostridium tetani*, and *Mycobacterium tuberculosis*. In still further examples, the heterologous antigen may be a tumor antigen including, for example, a tumor antigen related to acute myelogenous leukemia, chronic myelogenous leukemia, myelodysplastic syndrome, acute lymphoblastic leukemia, chronic lymphoblastic leukemia, non-Hodgkin's lymphoma, multiple myeloma, malignant melanoma, breast cancer, lung cancer, ovarian cancer, prostate cancer, pancreatic cancer, colon cancer, anal or rectal cancer, renal cell carcinoma (RCC), and germ cell tumors. In still further examples, the heterologous antigen may be a tissue-specific antigen or a host self-antigen including, for example, an antigen derived from the variable region of a T cell receptor, an antigen derived from the variable region of a B cell receptor, a sperm antigen, or an egg antigen.

In some examples, the vector does not express an active UL82 (pp71), UL79, US11, or other CMV protein due to the presence of a mutation in the nucleic acid sequence encoding UL82 (pp71), UL79, US11, or other CMV proteins, including homologs thereof or orthologs thereof (homologous genes of CMVs that infect other species). In some embodiments, the vector does not express an active UL82 (pp71) protein or an active UL79 protein, or orthologs thereof. In some embodiments, the vector does not express an active UL82 (pp71) protein or an active US11 protein, or orthologs thereof. In some embodiments, the vector does not express an active UL79 protein or an active US11 protein, or orthologs thereof. In some embodiments, the vector does not express an active UL79 protein, an active UL82 (pp71) protein, or an active US11 protein, or orthologs thereof. The mutation may be any mutation that results in a lack of expression of the active protein. Such mutations may include point mutations, frameshift mutations, deletions of less than all of the sequence that encodes the protein (truncation mutations), or deletions of all of the nucleic acid sequence that encodes the protein, or any other mutations.

Also disclosed herein are methods of generating CD8+ T cell responses to heterologous antigens in a subject. The methods involve administering an effective amount of a CMV vector to the subject. The CMV vector has a nucleic acid sequence that encodes at least one heterologous antigen and a nucleic acid sequence that serves as a miRNA response element (MRE) for a miRNA that is expressed by myeloid cells. The MRE is operably linked to a CMV gene that is essential or augmenting for CMV growth in vivo.

In some examples, the CMV vectors also contain nucleic acid sequences that encode an active UL128 protein and an active UL130 protein. These vectors may be used to elicit a CD8+ T cell response that is characterized by having at least 10% of the CD8+ T cells directed against epitopes presented by Class II MHC. In some embodiments, at least 20%, at least 30%, at least 40%, at least 50%, at least 60%, or at least 75%, of the CD8+ T cells are restricted by Class II MHC. This is an unpredictable result because previous studies showed that Class II MHC restricted CD8+ T cells were generated in CMV lacking UL128 and UL130 (Hansen S G et al, *Science* 340, 1237874 (2013); incorporated by reference herein). Less than 10% of the CD8+ T cells are restricted by MHC-E.

In some examples, the CMV vectors do not express an active UL128 and UL130 gene due to the presence of a mutation in the nucleic acid sequence encoding UL128 and UL130 and/or other CMV proteins including homologs thereof or orthologs thereof (homologous genes of CMVs that infect other species). The mutation may be any mutation that results in a lack of expression of the active protein. Such mutations may include point mutations, frameshift mutations, deletions of less than all of the sequence that encodes the protein (truncation mutations), or deletions of all of the nucleic acid sequence that encodes the protein, or any other mutations. These vectors may be used to elicit a CD8+ T cell response that is characterized by having less than 10% of the CD8+ T cells restricted by MHC-I and at least 10%, at least 20%, at least 30%, at least 40%, at least 50%, at least 60%, or at least 75%, of the CD8+ T cells are restricted by Class II MHC. These vectors may also be used to elicit CD8+ T cell responses to MHC-II supertopes, e.g., peptides presented by disparate MHC-II molecules to CD8+ T cells. Supertopes are thus recognized by individuals that do not share the same MHC-II alleles.

In further examples, the methods involve administering an effective amount of a second CMV vector, the second CMV vector comprising a nucleic acid sequence that encodes a second heterologous antigen to the subject. This second vector may be any CMV vector. The second heterologous antigen may be any heterologous antigen, including a heterologous antigen identical to the heterologous antigen in the first CMV vector. The second CMV vector may be administered at any time relative to the administration of the first CMV vector including before, concurrently with, or after the administration of the first CMV vector. This includes administration of the second vector any number of months, days, hours, minutes or seconds before or after the first vector.

Human or animal CMV vectors, when used as expression vectors, are innately non-pathogenic in the selected subjects such as humans. In some embodiments, the CMV vectors have been modified to render them non-pathogenic by limiting intra-host and host-to-host spread in the selected subjects.

A heterologous antigen may be any protein or fragment thereof that is not derived from CMV, including cancer antigens, pathogen specific antigens, model antigens (such as lysozyme KLH, or ovalbumin), tissue-specific antigens, host self-antigens, or any other antigen.

Pathogen specific antigens may be derived from any human or animal pathogen. The pathogen may be a viral pathogen, a bacterial pathogen, or a parasite, and the antigen may be a protein derived from the viral pathogen, bacterial pathogen, or parasite. The parasite may be an organism or disease caused by an organism. For example, the parasite may be a protozoan organism, a protozoan organism causing a disease, a helminth organism or worm, a disease caused by a helminth organism, an ectoparasite, or a disease caused by an ectoparasite.

The antigen may be a protein derived from cancer. These cancers include, but are not limited to, acute myelogenous leukemia, chronic myelogenous leukemia, myelodysplastic syndrome, acute lymphoblastic leukemia, chronic lymphoblastic leukemia, non-Hodgkin's lymphoma, multiple myeloma, malignant melanoma, breast cancer, lung cancer, ovarian cancer, prostate cancer, pancreatic cancer, colon cancer, renal cell carcinoma (RCC), and germ cell tumors.

The antigen may be a host self-antigen. Host self-antigens include, but are not limited to, antigens derived from the variable region of a T cell receptor or from the variable region of a B cell receptor. The antigen may be a tissue-specific antigen. Tissue-specific antigens include, but are not limited to, sperm antigens or egg antigens.

The CMV vectors disclosed herein may be used as an immunogenic, immunological, or vaccine composition containing the recombinant CMV virus or vector and a pharmaceutically acceptable carrier or diluent. An immunological composition containing the recombinant CMV virus or vector (or an expression product thereof) elicits an immunological response-local or systemic. The response may, but need not be, protective. An immunogenic composition containing the recombinant CMV virus or vector (or an expression product thereof) likewise elicits a local or systemic immunological response which may, but need not be, protective. A vaccine composition elicits a local or systemic protective response. Accordingly, the terms "immunological composition" and "immunogenic composition" include a "vaccine composition" (as the two former terms may be protective compositions).

The CMV vectors disclosed herein may be used in methods of inducing an immunological response in a subject comprising administering to the subject an immunogenic, immunological, or vaccine composition comprising the recombinant CMV virus or vector and a pharmaceutically acceptable carrier or diluent. For purposes of this specification, the term "subject" includes all animals, including non-human primates and humans, while "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

The CMV vectors disclosed herein may be used in therapeutic compositions containing the recombinant CMV virus or vector and a pharmaceutically acceptable carrier or diluent. The CMV vectors disclosed herein may be prepared by inserting DNA comprising a sequence that encodes the heterologous antigen into an essential or non-essential region of the CMV genome. The method may further comprise deleting one or more regions from the CMV genome. The method may comprise in vivo recombination. Thus, the method may comprise transfecting a cell with CMV DNA in a cell-compatible medium in the presence of donor DNA comprising the heterologous DNA flanked by DNA sequences homologous with portions of the CMV genome, whereby the heterologous DNA is introduced into the genome of the CMV, and optionally then recovering CMV modified by the in vivo recombination.

The method may also comprise cleaving CMV DNA to obtain cleaved CMV DNA, ligating the heterologous DNA to the cleaved CMV DNA to obtain hybrid CMV-heterologous DNA, transfecting a cell with the hybrid CMV-heterologous DNA, and optionally then recovering CMV modified by the presence of the heterologous DNA. Since in vivo recombination is comprehended, the method accordingly also provides a plasmid comprising donor DNA not naturally occurring in CMV encoding a polypeptide foreign to CMV, the donor DNA is within a segment of CMV DNA that would otherwise be co-linear with an essential or non-essential region of the CMV genome such that DNA from an essential or nonessential region of CMV is flanking the donor DNA. The heterologous DNA may be inserted into CMV to generate the recombinant CMV in any orientation that yields stable integration of that DNA, and expression thereof, when desired.

The DNA encoding the heterologous antigen in the recombinant CMV vector may also include a promoter. The promoter may be from any source such as a herpes virus, including an endogenous cytomegalovirus (CMV) promoter, such as a human CMV (HCMV), rhesus macaque CMV (RhCMV), murine CMV (MCMV), or other CMV promoter. The promoter may also be a non-viral promoter such as the EF1α promoter. The promoter may be a truncated transcriptionally active promoter which comprises a region transactivated with a transactivating protein provided by the virus and the minimal promoter region of the full-length promoter from which the truncated transcriptionally active promoter is derived. The promoter may be composed of an association of DNA sequences corresponding to the minimal promoter and upstream regulatory sequences. A minimal promoter is composed of the CAP site plus TATA box (minimum sequences for basic level of transcription; unregulated level of transcription); "upstream regulatory sequences" are composed of the upstream element(s) and enhancer sequence(s). Further, the term "truncated" indicates that the full-length promoter is not completely present, i.e., that some portion of the full-length promoter has been removed. And, the truncated promoter may be derived from a herpesvirus such as MCMV or HCMV, e.g., HCMV-IE or MCMV-IE. There may be up to a 40% and even up to a 90% reduction in size, from a full-length promoter, based upon base pairs.

The promoter may also be a modified non-viral promoter. As to HCMV promoters, reference is made to U.S. Pat. Nos. 5,168,062 and 5,385,839. As to transfecting cells with plasmid DNA for expression therefrom, reference is made to Feigner et al. (1994), *J. Biol. Chem.* 269, 2550-2561. And, as to direct injection of plasmid DNA as a simple and effective method of vaccination against a variety of infectious diseases reference is made to *Science,* 259:1745-49, 1993. It is therefore within the scope of this disclosure that the vector may be used by the direct injection of vector DNA.

Also disclosed is an expression cassette that may be inserted into a recombinant virus or plasmid comprising the truncated transcriptionally active promoter. The expression cassette may further include a functional truncated polyadenylation signal; for instance an SV40 polyadenylation signal which is truncated, yet functional. Considering that nature provided a larger signal, it is indeed surprising that a truncated polyadenylation signal is functional. A truncated polyadenylation signal addresses the insert size limit problems of recombinant viruses such as CMV. The expression cassette may also include heterologous DNA with respect to the virus or system into which it is inserted; and that DNA may be heterologous DNA as described herein.

As to antigens for use in vaccine or immunological compositions, see also *Stedman's Medical Dictionary* (24th edition, 1982), e.g., definition of vaccine (for a list of antigens used in vaccine formulations); such antigens or epitopes of interest from those antigens may be used. As to heterologous antigens, one of ordinary skill in the art may select a heterologous antigen and the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

One method to determine T epitopes of an antigen involves epitope mapping. Overlapping peptides of the heterologous antigen are generated by oligo-peptide synthesis. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules.

An immune response to a heterologous antigen is generated, in general, as follows: T cells recognize proteins only when the protein has been cleaved into smaller peptides and is presented in a complex called the "major histocompatibility complex (MHC)" located on another cell's surface. There are two classes of MHC complexes-class I and class II, and each class is made up of many different alleles. Different species, and individual subjects have different types of MHC complex alleles; they are said to have a different MHC type.

It is noted that the DNA comprising the sequence encoding the heterologous antigen may itself include a promoter for driving expression in the CMV vector or the DNA may be limited to the coding DNA of the heterologous antigen.

This construct may be placed in such an orientation relative to an endogenous CMV promoter that it is operably linked to the promoter and is thereby expressed. Further, multiple copies of DNA encoding the heterologous antigen or use of a strong or early promoter or early and late promoter, or any combination thereof, may be done so as to amplify or increase expression. Thus, the DNA encoding the heterologous antigen may be suitably positioned with respect to a CMV-endogenous promoter, or those promoters may be translocated to be inserted at another location together with the DNA encoding the heterologous antigen. Nucleic acids encoding more than one heterologous antigen may be packaged in the CMV vector.

Further, disclosed are pharmaceutical and other compositions containing the disclosed CMV vectors. Such pharmaceutical and other compositions may be formulated so as to be used in any administration procedure known in the art. Such pharmaceutical compositions may be via a parenteral route (intradermal, intramuscular, subcutaneous, intravenous, or others). The administration may also be via a mucosal route, e.g., oral, nasal, genital, etc.

The disclosed pharmaceutical compositions may be prepared in accordance with standard techniques well known to those of ordinary skill in the pharmaceutical arts. Such compositions may be administered in dosages and by techniques well known to those of ordinary skill in the medical arts taking into consideration such factors as the breed or species, age, sex, weight, and condition of the particular patient, and the route of administration. The compositions may be administered alone, or may be co-administered or sequentially administered with other CMV vectors or with other immunological, antigenic or vaccine or therapeutic compositions. Such other compositions may include purified native antigens or epitopes or antigens or epitopes from the expression by a recombinant CMV or another vector system; and are administered taking into account the aforementioned factors.

Examples of compositions include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant may be in admixture with a suitable carrier, diluent, or excipient such as sterile water, physiological saline, glucose or the like.

Antigenic, immunological, or vaccine compositions typically may contain an adjuvant and an amount of the CMV vector or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al. *J. Immunol.* 147:410-415 (1991), encapsulation of the protein within a proteoliposome as described by Miller et al., *J. Exp. Med.* 176:1739-1744 (1992), and encapsulation of the protein in lipid vesicles such as Novasome lipid vesicles (Micro Vescular Systems, Inc., Nashua, N.H.) may also be used.

The composition may be packaged in a single dosage form for immunization by parenteral (e.g., intramuscular, intradermal or subcutaneous) administration or orifice administration, e.g., perlingual (e.g., oral), intragastric, mucosal including intraoral, intraanal, intravaginal, and the like administration. And again, the effective dosage and route of administration are determined by the nature of the composition, by the nature of the expression product, by expression level if recombinant CMV is directly used, and by known factors, such as breed or species, age, sex, weight, condition and nature of host, as well as $LD_{50}$ and other screening procedures which are known and do not require undue experimentation. Dosages of expressed product may range from a few to a few hundred micrograms, e.g., 5 to 500 µg. The CMV vector may be administered in any suitable amount to achieve expression at these dosage levels. In non-limiting examples: CMV vectors may be administered in an amount of at least $10^2$ pfu; thus, CMV vectors may be administered in at least this amount; or in a range from about $10^2$ pfu to about $10^7$ pfu. Other suitable carriers or diluents may be water or a buffered saline, with or without a preservative. The CMV vector may be lyophilized for resuspension at the time of administration or may be in solution. "About" may mean within 1%, 5%, 10% or 20% of a defined value.

It should be understood that the proteins and the nucleic acids encoding them of the present disclosure may differ from the exact sequences illustrated and described herein. Thus, the disclosure contemplates deletions, additions, truncations, and substitutions to the sequences shown, so long as the sequences function in accordance with the methods of the disclosure. In this regard, substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine threonine, and tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the proteins described but possessing minor amino acid substitutions that do not substantially affect the immunogenicity of the protein are, therefore, within the scope of the disclosure.

The nucleotide sequences of the present disclosure may be codon optimized, for example the codons may be optimized for use in human cells. For example, any viral or bacterial sequence may be so altered. Many viruses, including HIV and other lentiviruses, use a large number of rare codons and, by altering these codons to correspond to codons commonly used in the desired subject, enhanced expression of the heterologous antigen may be achieved as described in Andre et al., *J. Virol.* 72:1497-1503, 1998.

Nucleotide sequences encoding functionally and/or antigenically equivalent variants and derivatives of the CMV vectors and the glycoproteins included therein are contemplated. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/ alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

Sequence identity or homology is determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, *Proc. Natl. Acad. Sci. USA* 1990; 87: 2264-2268, modified as in Karlin & Altschul, *Proc. Natl. Acad. Sci. USA* 1993; 90: 5873-5877.

Another example of a mathematical algorithm used for comparison of sequences is the algorithm of Myers & Miller, *CABIOS* 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may be used. Yet another useful algorithm for identifying regions of local sequence similarity and alignment is the FASTA algorithm as described in Pearson & Lipman, *Proc. Natl. Acad. Sci. USA* 1988; 85: 2444-2448.

Advantageous for use according to the present disclosure is the WU-BLAST (Washington University BLAST) version 2.0 software. WU-BLAST version 2.0 executable programs for several UNIX platforms may be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., *Methods in Enzymology* 266: 460-480; Altschul et al., *Journal of Molecular Biology* 1990; 215: 403-410; Gish & States, 1993; *Nature Genetics* 3: 266-272; Karlin & Altschul, 1993; *Proc. Natl. Acad. Sci. USA* 90: 5873-5877; all of which are incorporated by reference herein).

The various recombinant nucleotide sequences and antibodies and/or antigens of the disclosure are made using standard recombinant DNA and cloning techniques. Such techniques are well known to those of ordinary skill in the art. See for example, *"Molecular Cloning: A Laboratory Manual"*, second edition (Sambrook et al. 1989).

The nucleotide sequences of the present disclosure may be inserted into "vectors." The term "vector" is widely used and understood by those of ordinary skill in the art, and as used herein the term "vector" is used consistent with its meaning to those of ordinary skill in the art. For example, the term "vector" is commonly used by those of ordinary skill in the art to refer to a vehicle that allows or facilitates the transfer of nucleic acid molecules from one environment to another or that allows or facilitates the manipulation of a nucleic acid molecule.

Any vector that allows expression of the viruses of the present disclosure may be used in accordance with the present disclosure. In certain embodiments, the disclosed viruses may be used in vitro (such as using cell-free expression systems) and/or in cultured cells grown in vitro in order to produce the encoded heterologous antigen (e.g., pathogen specific antigens, HIV antigens, tumor antigens, and antibodies) which may then be used for various applications such as in the production of proteinaceous vaccines. For such applications, any vector that allows expression of the virus in vitro and/or in cultured cells may be used.

For the disclosed heterologous antigens to be expressed, the protein coding sequence of the heterologous antigen should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" may be any nucleic acid element, such as, but not limited to promoters, enhancers, IRES, introns, miRNA recognition elements (MREs) and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the disclosure lead to the expression of the encoded protein. The expression of the transgenes of the present disclosure may be under the control of a constitutive promoter or of an inducible promoter, which initiates transcription only when exposed to some particular external stimulus, such as, without limitation, antibiotics such as tetracycline, hormones such as ecdysone, or heavy metals. The promoter may also be specific to a particular cell-type, tissue or organ. Many suitable promoters and enhancers are known in the art, and any such suitable promoter or enhancer may be used for expression of the transgenes of the disclosure. For example, suitable promoters and/or enhancers may be selected from the Eukaryotic Promoter Database (EPDB).

The disclosure relates to a recombinant viral vector expressing a heterologous protein antigen. In some examples, the antigen is an HIV antigen. Advantageously, the HIV antigens include, but are not limited to, the HIV antigens discussed in U.S. Pub. Nos. 2008/0199493 A1 and 2013/0136768 A1, both of which are incorporated by reference herein. HIV, nucleic acid or immunogenic fragments thereof, may be utilized as an HIV protein antigen. For example, the HIV nucleotides discussed in U.S. Pub. Nos. 2008/0199493 A1 and 2013/0136768 A1 may be used. Any antigen recognized by an HIV antibody may be used as an HIV protein antigen. The protein antigen may also be an SIV antigen. For example, the SIV antigens discussed in U.S. Pub. Nos. 2008/0199493 A1 and 2013/0136768 A1 may be used.

The vectors used in accordance with the present disclosure may contain a suitable gene regulatory region, such as a promoter or enhancer, such that the antigens may be expressed.

Expressing antigens of the disclosure in vivo in a subject, for example in order to generate an immune response against an HIV-1 antigen and/or protective immunity against HIV-1, expression vectors that are suitable for expression on that subject, and that are safe for use in vivo, should be chosen. In some examples, it may be desired to express the antibodies and/or antigens in a laboratory animal, such as for pre-clinical testing of the HIV-1 immunogenic compositions and vaccines of the disclosure. In other examples, one may express the antigens in human subjects, such as in clinical trials and for actual clinical use of the immunogenic compositions and vaccine of the disclosure.

The CMV vectors described herein may contain mutations that may prevent intrahost and host to host spread, thereby rendering the virus unable to spread in or infect immunocompromised or other subjects that could face complications as a result of CMV infection. The CMV vectors described herein may also contain mutations that result in the presentation of immunodominant and nonimmunodominant epitopes as well as unconventional MHC restriction. However, mutations in the CMV vectors described herein do not affect the ability of the vector to reinfect a subject that has been previously infected with CMV. Such CMV mutations are described in, for example, US Patent Publications 2013-0136768; 2010-0142823; 2014-0141038; and PCT application publication WO 2014/138209, all of which are incorporated by reference herein.

The disclosed CMV vectors may be administered in vivo, for example where the aim is to produce an immunogenic response, including a CD8+ immune response, including an immune response characterized by a high percentage of the CD8$^+$ T cell response being restricted by MHC Class II (or a homolog or ortholog thereof). For example, in some examples it may be desired to use the disclosed CMV vectors in a laboratory animal, such as rhesus macaques for pre-clinical testing of immunogenic compositions and vaccines using RhCMV. In other examples, it will be desirable to use the disclosed CMV vectors in human subjects, such as in clinical trials and for actual clinical use of the immunogenic compositions using HCMV.

For such in vivo applications the disclosed CMV vectors are administered as a component of an immunogenic composition further comprising a pharmaceutically acceptable carrier. The immunogenic compositions of the disclosure are useful to stimulate an immune response against the heterologous antigen, including a pathogen specific antigen and may be used as one or more components of a prophylactic or therapeutic vaccine against HIV-1 for the prevention, amelioration or treatment of AIDS. The nucleic acids and vectors of the disclosure are particularly useful for providing genetic vaccines, i.e. vaccines for delivering the nucleic acids encoding the antigens of the disclosure to a subject, such as a human, such that the antigens are then expressed in the subject to elicit an immune response.

Immunization schedules (or regimens) are well known for animals (including humans) and may be readily determined for the particular subject and immunogenic composition. Hence, the immunogens may be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. In a particularly advantageous embodiment of the present disclosure, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks or 70 weeks. The immunization regimes typically have from 1 to 6 administrations of the immunogenic composition, but may have as few as one or two or four. The methods of inducing an immune response may also include administration of an adjuvant with the immunogens. In some instances, annual, biannual or other long interval (5-10 years) booster immunization may supplement the initial immunization protocol. The present methods also include a variety of prime-boost regimens. In these methods, one or more priming immunizations are followed by one or more boosting immunizations. The actual immunogenic composition may be the same or different for each immunization and the type of immunogenic composition (e.g., containing protein or expression vector), the route, and formulation of the immunogens may also be varied. For example, if an expression vector is used for the priming and boosting steps, it may either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of ordinary skill in the art that there are several permutations and combinations that are encompassed using the DNA, bacterial and viral expression vectors of the disclosure to provide priming and boosting regimens. CMV vectors may be used repeatedly while expressing different antigens derived from different pathogens.

EXAMPLES

Example 1—CMV Vectors Comprising MicroRNA Recognition Elements (MRE)

In order to limit the ability of the RhCMV-based vectors to replicate in myeloid lineage cells, CMV was engineered to express the myeloid-specific miRNA miR-142 3p. It was hypothesized that insertion of miR-142 3p target sites into the 3' UTRs of essential RhCMV genes would result in an inhibition of viral replication due to degradation of the targeted viral mRNAs in cells that express the miRNA.

The miR-142 3p miRNA is highly expressed in rhesus macaque macrophages derived from the peripheral blood of three animals (FIG. 1). Whole blood was fractionated, and CD14-positive cells were isolated using magnetic cell sorting with CD14 beads. CD14-positive cells were plated in RPMI with M-CSF or in a 1:1 mix of RPMI and M-CSF-conditioned RPMI. After 7 days, the CD14-positive cells adhered to the tissue culture plate and differentiated into more mature macrophages. These cells were harvested in Trizol and RNA was isolated using standard procedures. RNA from rhesus fibroblasts was also isolated and qRT-PCR for miR-142 3p was performed on all samples. These data demonstrate that rhesus macaque myeloid lineage cells express much higher levels of miR-142 3p compared to rhesus fibroblasts and provides a rationale for using this miRNA to target essential RhCMV transcripts.

Figure 2:
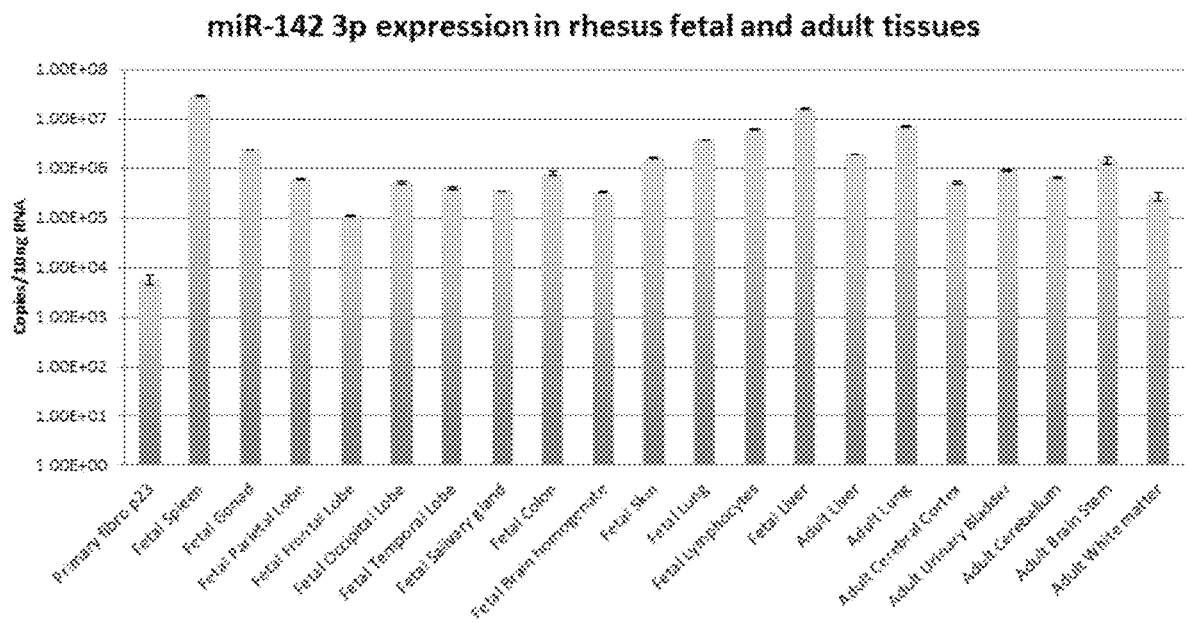
FIG. 2 is a bar graph showing miR-142-3p expression in the indicated cell types and tissues isolated from rhesus macaques; in accordance with various embodiments.

In order to better understand the expression of miR-142 3p in other cell types RNA was isolated from a variety of homogenized fetal and adult tissues using Trizol (FIG. 2). qRT-PCR for miR-142-3p was performed using a miRNA mimic as a standard control. The highest expression of miR-142-3p (~$10^7$ copies/10 ng of RNA) was detected in tissues that normally contain large numbers of myeloid cells, including fetal spleen, lymphocytes and liver, as well as in the adult lung. Thus miR-142-3p expression is detectable in a variety of tissues. However it was unclear if the miRNA arose from resident or circulating myeloid-lineage cells or is expressed from other cell types in the tissue. These data demonstrate that limiting replication of the vaccine vector in myeloid-lineage cells may prevent the dissemination of the vector to a wide variety of tissues.

Since the above data demonstrates that miR-142-3p is highly expressed in rhesus macaque myeloid-lineage cells, vaccine vector tropism was altered by using miR-142-3p as a host restriction factor. RhCMV 68-1 (UL128/UL130-deleted) and 68-1.2 (UL128/UL130-intact) viruses containing miR-142-3p target sites within the 3' UTRs of Rh156 (an essential immediate early gene homologous to HCMV IE2) and Rh108 (an essential early gene homologous to HCMV UL79) were generated. These vectors additionally expressed a heterologous antigen derived from SIV, e.g., SIVgag or SIV retanef, by inserting this antigen under control of the EF1α promoter into the gene Rh211.

Figure 3A:
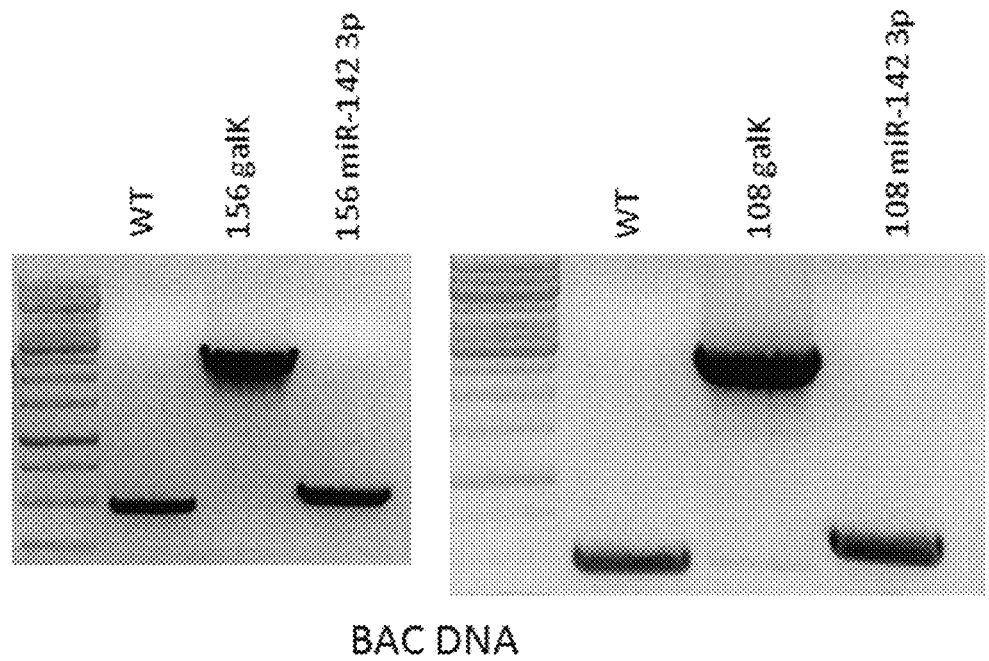
FIGS. 3A, 3B, 3C, and 3D collectively show the analysis of the recombinant RhCMV 68-1 RTN Rh156/Rh108 miR-142 3p mutant virus generated via galK recombination, in accordance with various embodiments.
Figure 3B:
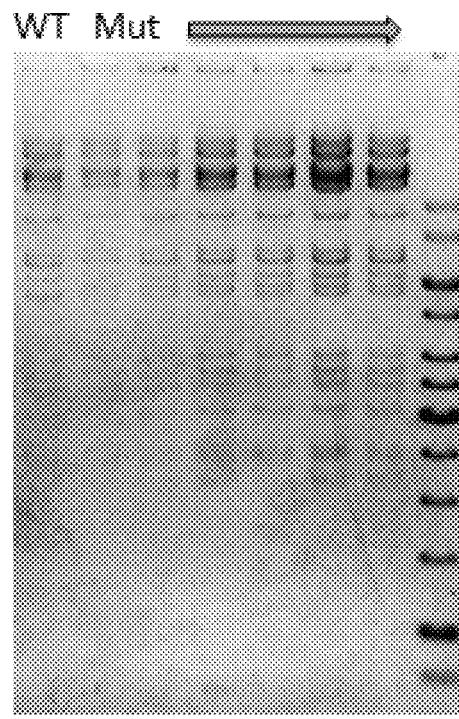
Figure 3C:
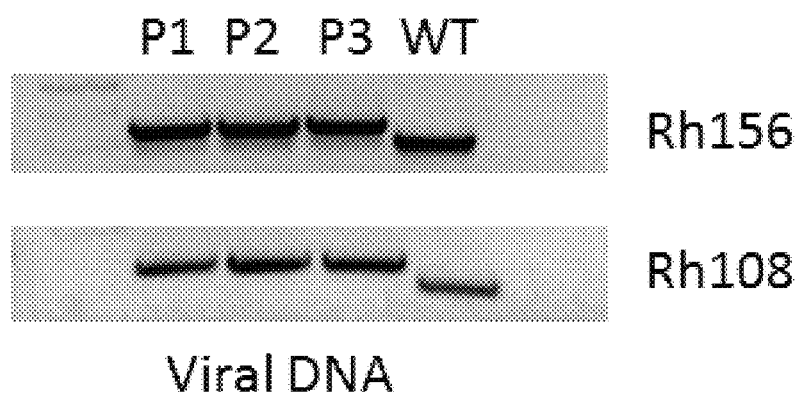
Figure 3D:
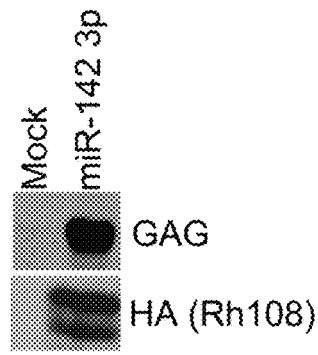
Figure 11:
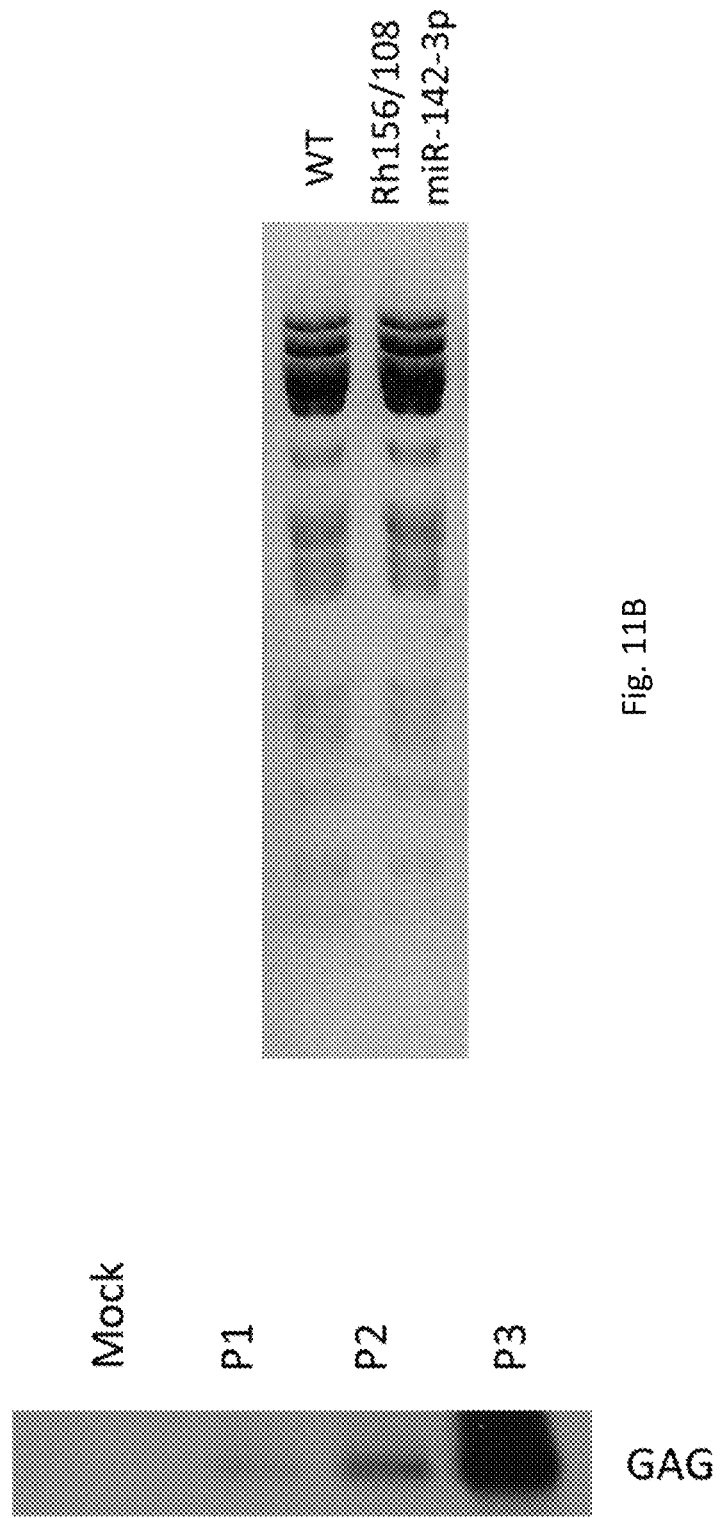
FIGS. 11A, 11B, and 11C collectively show the analysis of the recombinant RhCMV 68-1.2 GAG Rh156/Rh108 miR-142 3p mutant virus generated via galK recombination, in accordance with various embodiments.

In cells in which miR-142-3p levels are high, this virus will be severely limited for growth as miR-142-3p will bind to the 3' UTRs of Rh156 and Rh108 and degrade the mRNAs thus severely inhibiting viral replication. Using galK-mediated BAC recombination the galK selection cassette was inserted within the 3' UTR of Rh156 and then replaced with an artificial cassette containing 4 copies of the miR-142-3p binding site separated by 8 random nucleotides. A second series of recombinations was then performed, thereby inserting the galK cassette into the 3' UTR of Rh108 and replacing this with an artificial cassette as above (FIG. 10, 3A, 11A). Successful recombinations were confirmed using PCR with primers designed to regions flanking the insertion site and subsequent sequencing of the PCR products. The integrity of the BAC genome was assessed using XmaI digestion of purified BAC DNA followed by electrophoresis on agarose gels (FIG. 3B, 11B). Intact BAC DNA was subsequently electroporated into primary rhesus fibroblasts and individual viral plaques were isolated and propagated for a total of three passages. Viral DNA was isolated from supernatants at each stage and assessed for maintenance of the miR-142-3p cassette by PCR using primers flanking the site and sequencing of the PCR products (FIG. 3C, 11A).

Figure 4:
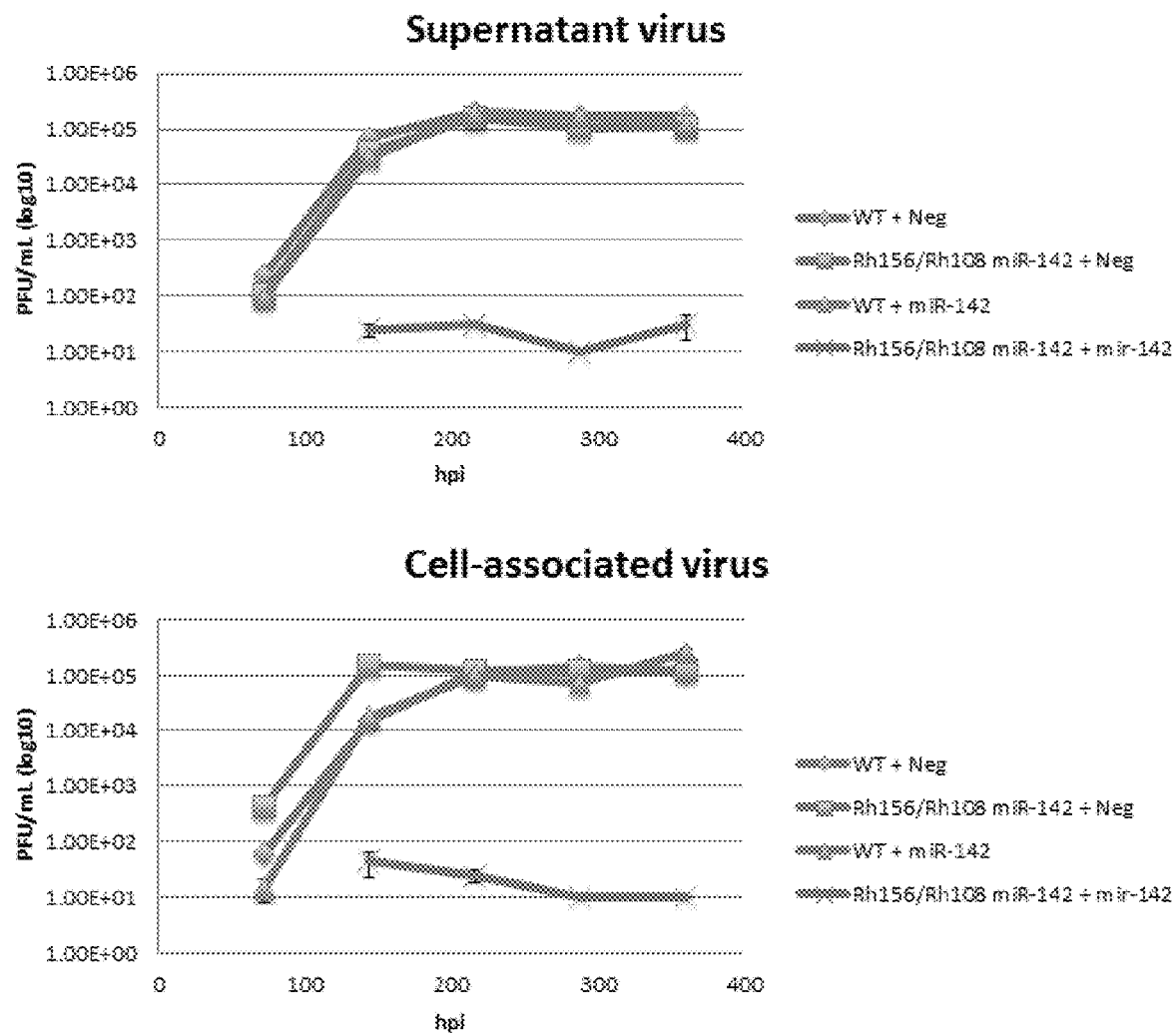
FIG. 4 is a set of two plots each showing a multi-step growth curve using 68-1 RTN Rh156/Rh108 miR-142 3p virus. Telomerized rhesus fibroblasts were transfected with negative control miRNA or a miR-142 3p RNA mimic. 24 hours after transfection, cells were infected with WT or the 68-1 RTN Rh156/Rh108 miR-142 3p viruses at an MOI of 0.01. Cells and supernatant were harvested at the indicated times and titered on rhesus fibroblasts, in accordance with various embodiments.
Figure 9:
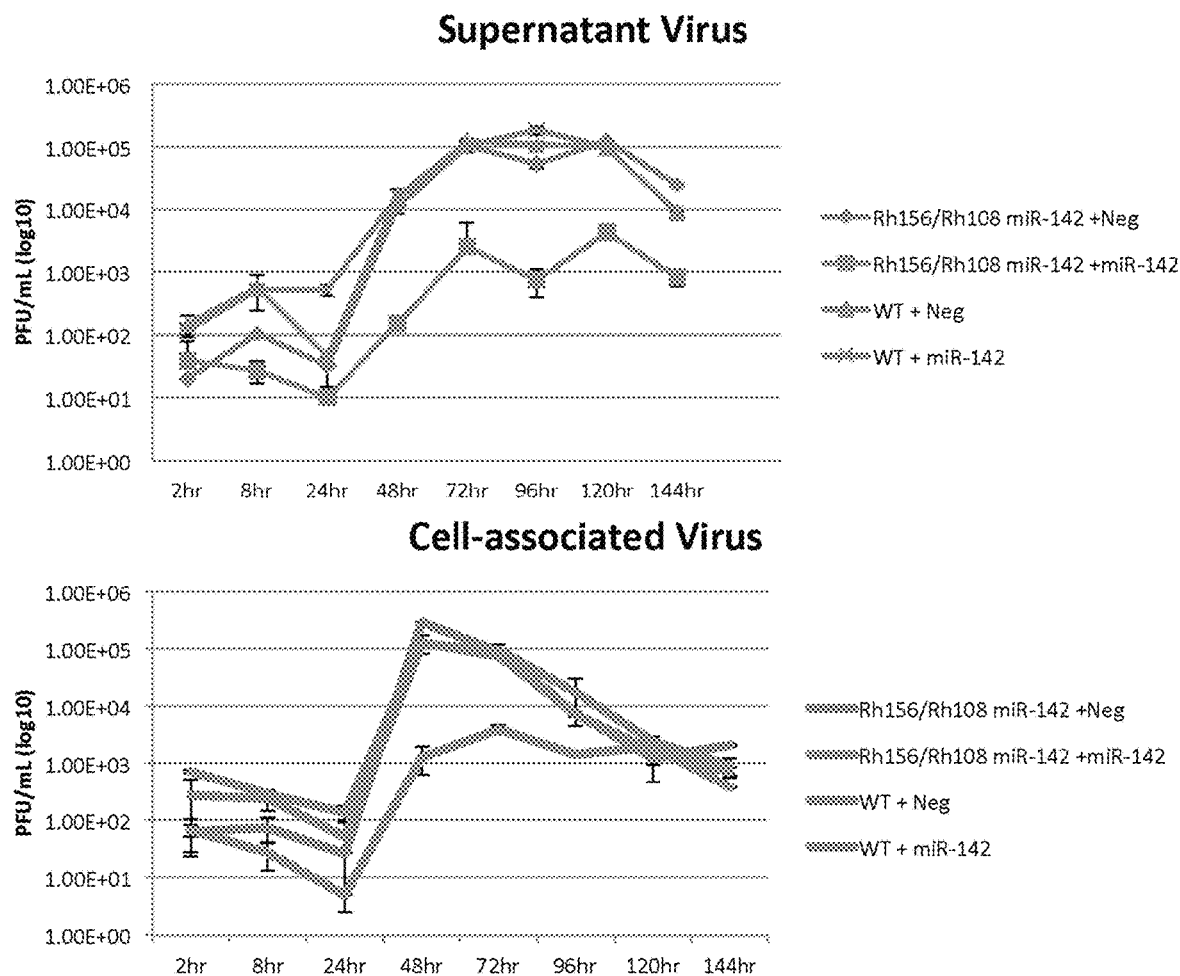
FIG. 9 is a set of two plots showing a growth curve using 68-1.2 RTN Rh156/Rh108 miR-142 3p virus. The procedure was otherwise performed as described for FIG. 4, in accordance with various embodiments.

The 68-1 and 68-1.2 Rh156/Rh108 virus produced from the above BAC recombinations was then analyzed for growth in the presence of miR-142-3p using a multi-step growth curve (FIGS. 4, 9). Rhesus fibroblasts were transfected using Lipofectamine 2000® with either negative control miRNA or a miR-142 3p mimic. Two days after transfection, cells were infected with either wild type 68-1 or the 68-1 Rh156/Rh108 miR-142-3p mutant at an MOI of 0.01 (FIG. 4). Alternatively, two days after transfection, cells were infected with either wild type 68-1.2 or the 68-1.2 Rh156/Rh108 miR-142-3p mutant at an MOI of 0.01 (FIG. 9). Cell pellets and supernatants were harvested at the indicated times and titered on primary rhesus fibroblasts. The presence of miR-142-3p mimic did not have any effect on the growth of WT virus. Importantly, the 68-1 Rh156/Rh108 miR-142-3p and 68-1.2 Rh156/Rh108 miR-142-3p mutant viruses did not show any growth defect in the presence of negative control miRNA but were severely inhibited for growth in the presence of miR-142-3p. For example, the presence of miR-142-3p reduced the viral titer of the 68-1 Rh156/Rh108 miR-142-3p mutant virus by up to 4 logs but had no effect on the viral titer of the wild type 68-1 virus (FIG. 4). Therefore, the virus with miR-142-3p target sites engineered into the 3' UTRs of two essential genes was severely limited for growth in the presence of the miRNA in vitro, indicating that this virus would be unable to replicate in cells of the myeloid lineage in vivo, where miR-142-3p levels are naturally high.

Figure 5:
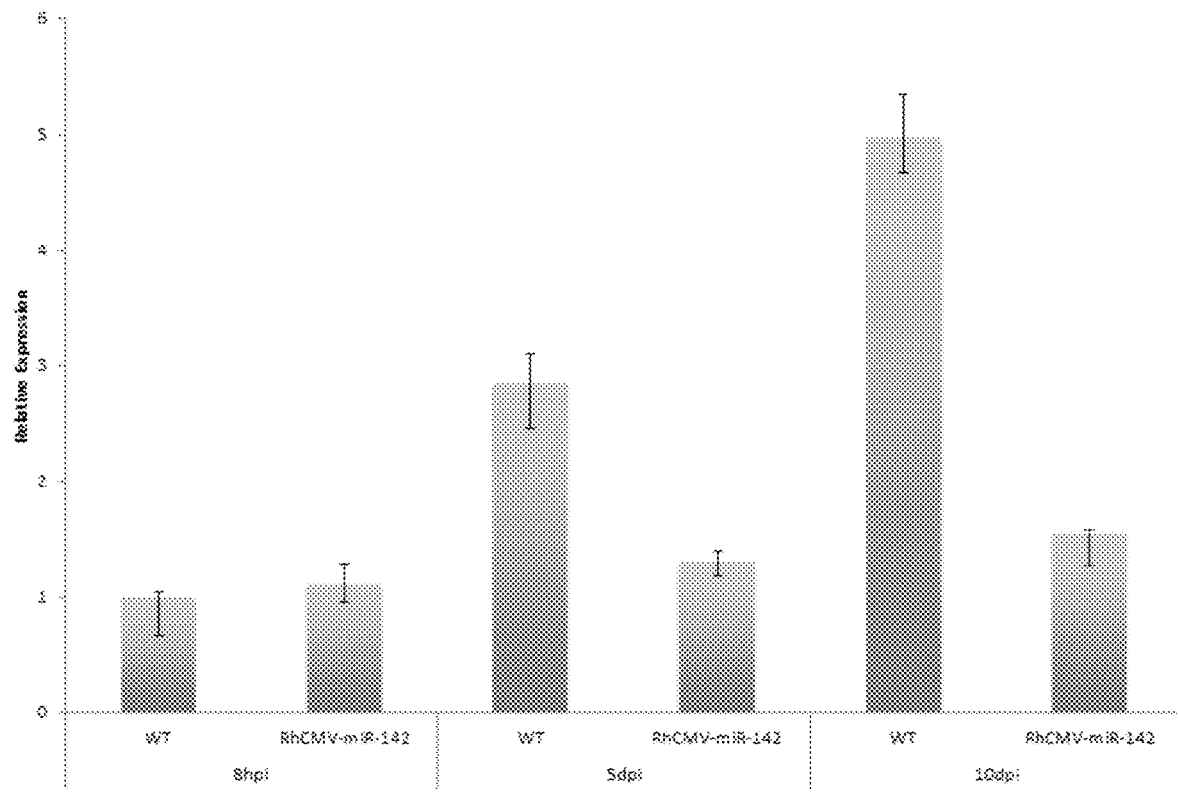
FIG. 5 is a bar graph of CD14+ cells isolated from rhesus macaque PBMCs using magnetic cell sorting. Cells were cultured in the presence of M-CSF-conditioned media for 7 days to allow for differentiation into macrophages. Cells were infected with WT 68-1 RTN or the 68-1 RTN Rh156/Rh108 miR-142 3p viruses at an MOI of 10. Viral DNA was harvested at the indicated timepoints and analyzed for Rh87 DNA levels by qPCR, in accordance with various embodiments.

The ability of the 68-1 Rh156/Rh108 miR-142-3p virus to replicate in ex vivo-derived rhesus macrophages was tested (FIG. 5). CD14+ cells from rhesus peripheral blood were isolated and differentiated as described above and infected with WT virus or the 68-1 Rh156/Rh108 miR-142 3p virus at an MOI of 10. Viral DNA levels were assessed using qPCR for Rh87 and GAPDH (as a control) at 8 hours as well as 5 and 10 days post-infection. While viral DNA levels increased over time in the cells infected with WT virus, little increase in viral DNA was detected in cells infected with the mutant virus. These data indicate that the miR-142-3p target sites inserted into the viral genome limit viral replication in rhesus macrophages and is further evidence that miR-142-3p acts as a strong host restriction factor in this cell type.

Figure 6:
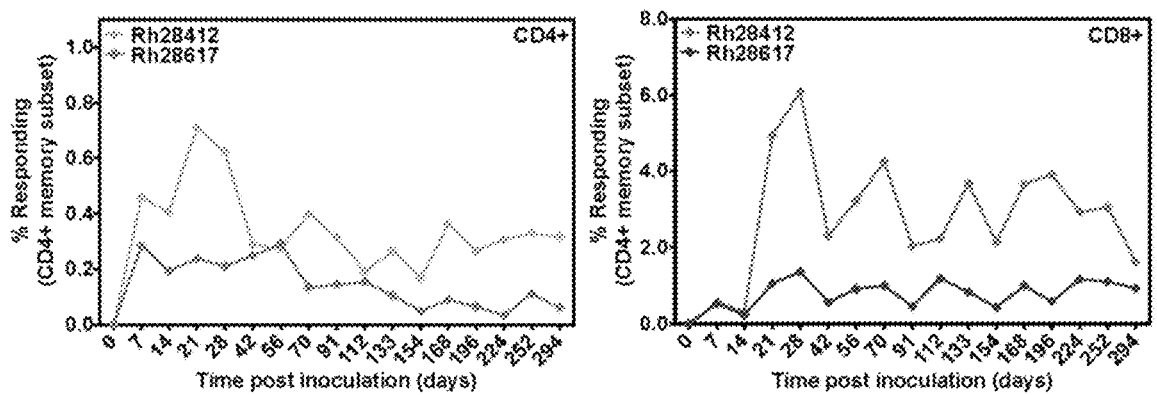
FIG. 6 is a set of two plots showing peripheral T cells responses to the SIV RTN antigen in animals infected with RhCMV-68-1-Rh156, 108 miR-142-SIVrtn, in accordance with various embodiments.

The immunogenicity of the miR-142-3p-restricted viruses was assessed in vivo. Initially, two adult animals were infected with the 68-1 RhCMV Rh156/Rh108 miR-142 3p/SIVrtn virus (which also contains the RTN transgene (a fusion of SIV rev, tat and nef) under control of the EF1α promoter) and peripheral blood CD4+ and CD8+ memory T cells were isolated and analyzed for responses to overlapping RTN peptides (FIG. 6). Both animals elicited robust, long-term CD4 and CD8 T cell responses to the transgene, indicating that overall immunogenicity of the vaccine vector is not compromised by the introduction of miR-142-3p target sites.

Figure 7:
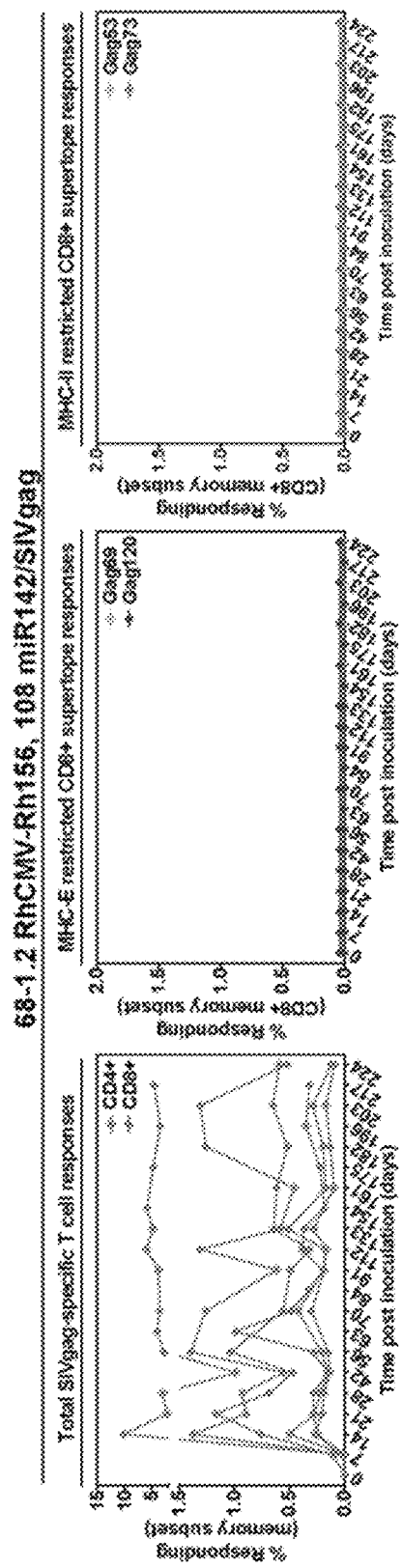
FIG. 7 is a set of three plots of CD8+ T cell responses in animals infected with 68-1.2 RhCMV-Rh156, 108 miR142/SIVgag, in accordance with various embodiments.
Figure 14:
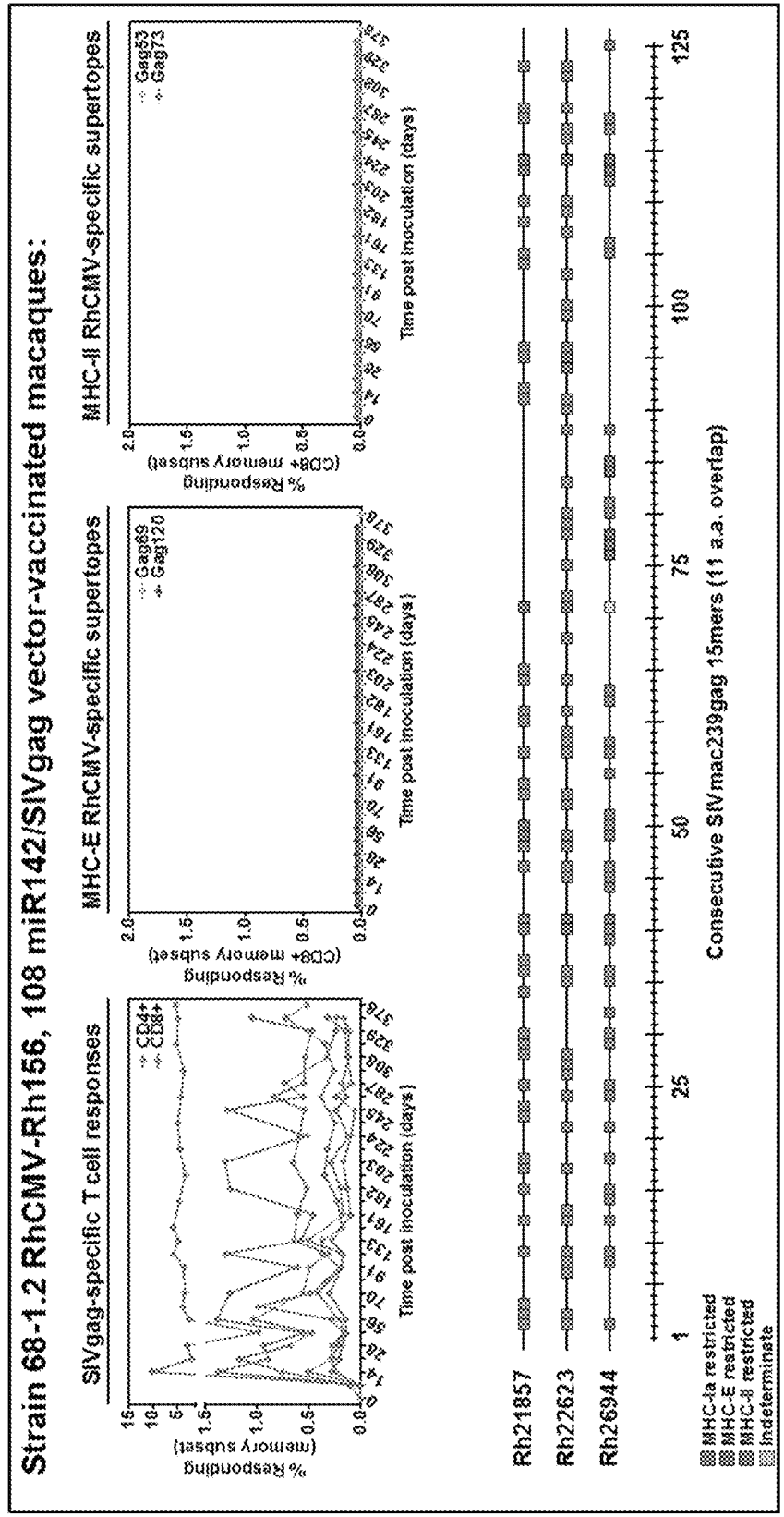
FIG. 14 is a set of three plots of CD8+ T cell responses in three animals infected with 68-1.2 RhCMV-Rh156, 108 miR142/SIVgag and an epitope MHC-restriction map of these animals, in accordance with various embodiments.

Peripheral T cell responses in animals infected with a 68-1.2 RhCMV Rh156/Rh108 miR-142-3p/SIVgag virus (which also contains the GAG transgene under control of the EF1α promoter) were then assessed. As seen in FIG. 7 and FIG. 14, this vaccine vector also elicits robust and long-term CD4+ and CD8+ T cell responses to the HIV gag protein encoded within the vaccine vector. It has been previously demonstrated that vaccine vectors lacking UL128 and UL130 (such as 68-1) elicit unconventional MHC-E and MHC-II restricted CD8 T cell responses, including so-called 'supertope' responses that are detectable in all infected animals. In vectors comprising intact UL128 and UL130 (such as 68-1.2) only conventional MHC-I restricted CD8 T cells are detected. FIGS. 7 and 14 demonstrate that both MHC-E and MHC-II restricted 'supertopes' are absent in animals infected with the 68-1.2 Rh156/Rh108 miR-142-3p virus.

Figure 8:
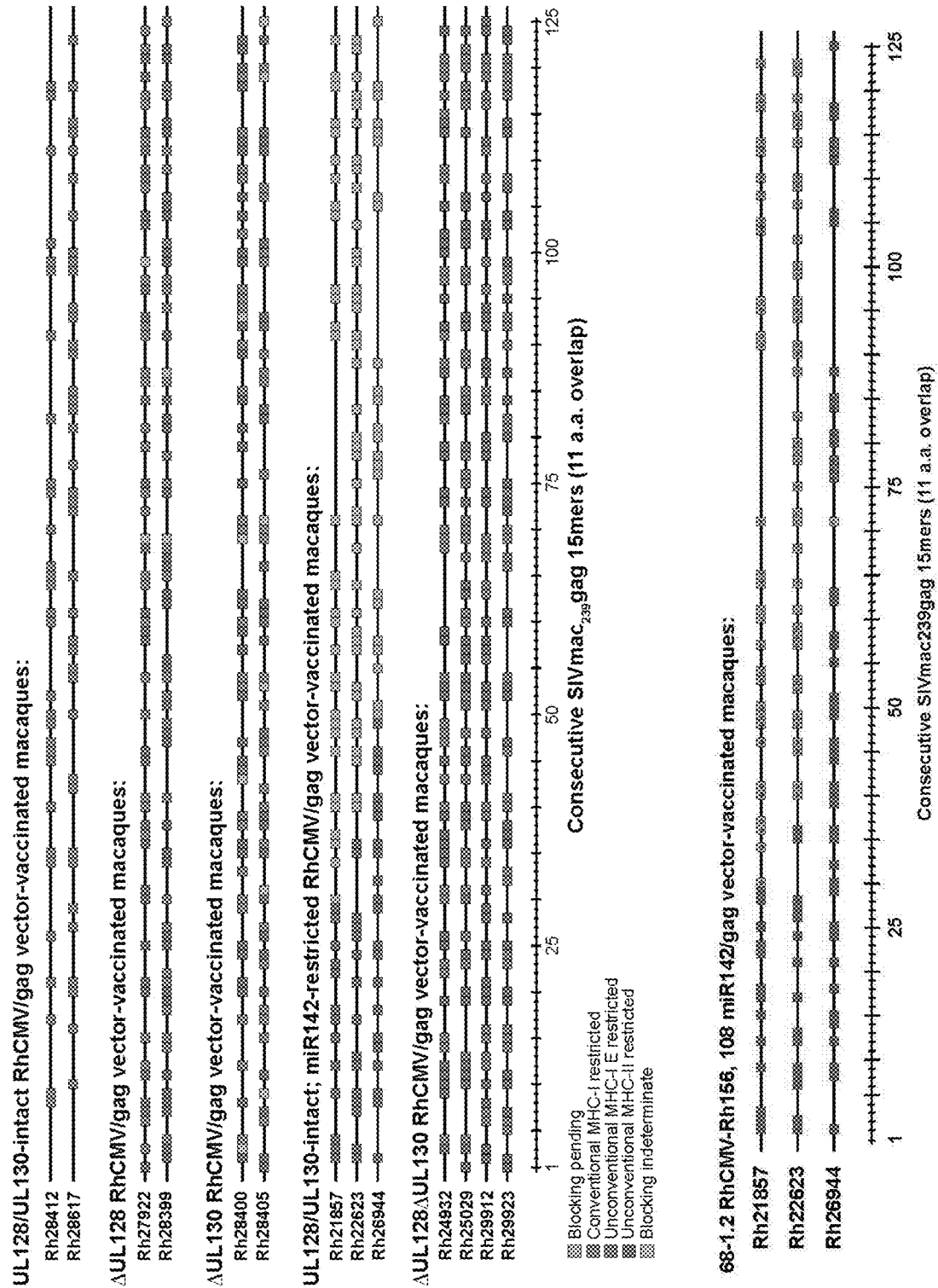
FIG. 8 is an epitope MHC-restriction map of animals of the indicated genotypes infected with the indicated vectors, in accordance with various embodiments.

Unexpectedly however, through further epitope mapping the T cell responses (FIGS. 8 and 14) it was determined that predominantly unconventional MHC-II restricted T cell responses were elicited by the 68-1.2 Rh156/Rh108 miR-142-3p/SIVgag virus, with relatively few MHC-Ia responses detected. By altering the myeloid cell tropism of 68-1.2 (UL128 and UL130-intact) the response was switched from conventional MHC-Ia to unconventional MHC-II restricted T cell responses, whereas both MHC-E responses and MHC-II 'supertope' responses are lacking. These data demonstrate an alternative method for eliciting the unconventional MHC-II restricted CD8 T cells through preventing viral replication in myeloid lineage cells. In addition, since macrophages play an important role in viral dissemination in vivo, using a miR-142 3p-based vector may improve vaccine safety.

Figure 12:
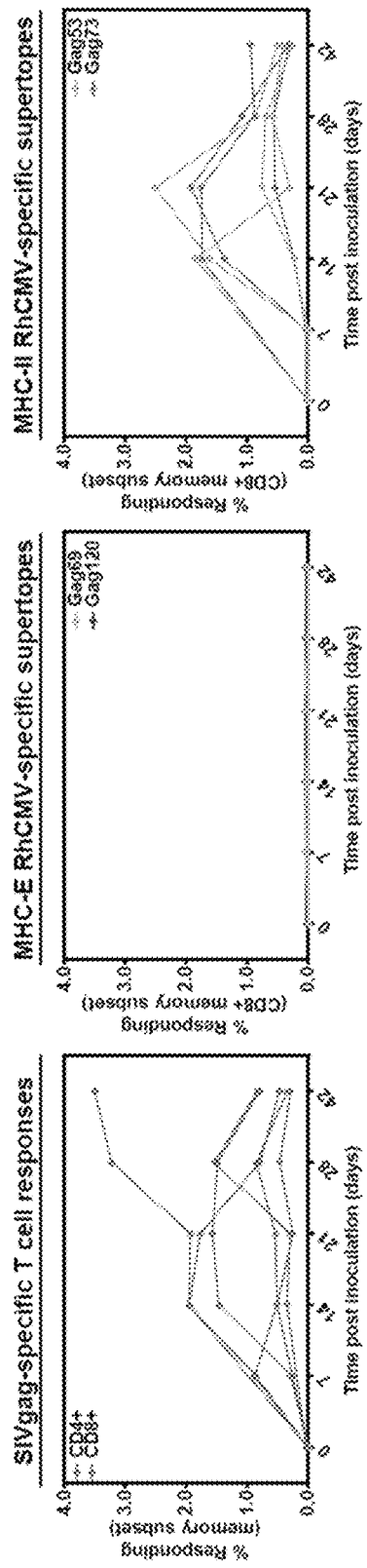
FIG. 12 is a set of three plots of T cell responses in animals infected with 68-1 RhCMV-Rh156, 108 miR142/SIVgag, in accordance with various embodiments.
Figure 13:
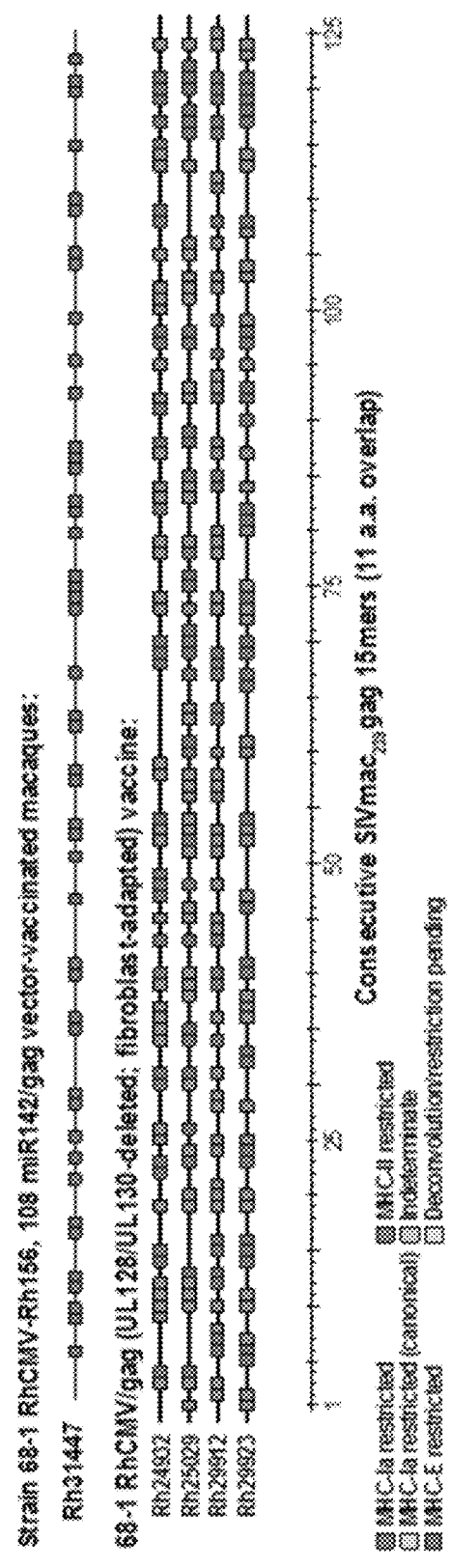
FIG. 13 is an epitope MHC-restriction map of an animal infected with 68-1 GAG Rh156/Rh108 miR-142 3p or four animals infected with 68-1 GAG, in accordance with various embodiments.

Peripheral T cell responses were also assessed in animals infected with a 68-1 RhCMV Rh156/Rh108 miR-142-3p/SIVgag virus (which also contains the GAG transgene under control of the EF1α promoter). As seen in FIG. 12, this vaccine vector also elicits robust and long-term CD4+ and CD8+ T cell responses to the HIV gag protein encoded within the vaccine vector. It has been previously demonstrated that 68-1-based vectors lacking UL128 and UL130 elicit unconventional MHC-E and MHC-II restricted CD8 T cell responses, including so-called 'supertope' responses that are detectable in all infected animals. However, FIG. 12 demonstrates that whereas the 68-1 RhCMV Rh156/Rh108 miR-142-3p virus retained its ability to elicit supertope responses to MHC-II, this vector failed to elicit supertope responses restricted by MHC-E. Furthermore, through further epitope mapping the T cell responses (FIG. 13) it was determined that the 68-1 RhCMV Rh156/Rh108 miR-142-3p vector exclusively elicited MHC-II restricted CD8+ T cell responses without any MHC-I-restricted or MHC-E-restricted CD8+ T cells. Thus, this vector elicits only MHC-II restricted CD8+ T cells. Since CD4+ T cells elicited by RhCMV are always restricted by MHC-II these data demonstrate that by introducing miR-142-3p targeting sites into vectors that lack UL128 and UL130 it is possible to generate a vaccine that elicits only MHC-II restricted responses, including MHC-II supertope responses that are shared among many different individuals.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with ordinary skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of generating an immune response to at least one heterologous antigen in a subject, the method comprising administering to the subject a cytomegalovirus (CMV) vector in an amount effective to elicit a CD8+ T cell response to the at least one heterologous antigen in the subject, wherein the CMV vector comprises:
   (a) a first nucleic acid sequence encoding at least one heterologous antigen;
   (b) a second nucleic acid sequence comprising a first microRNA recognition element (MRE) operably linked to a CMV gene that is essential or augmenting for CMV growth and wherein the MRE silences expression in presence of miR-142-3p;
   (c) a third nucleic acid sequence that encodes an active UL128 protein or ortholog thereof; and
   (d) a fourth nucleic acid sequence that encodes an active UL130 protein or ortholog thereof.

2. The method of claim 1, wherein at least 10% of the CD8+ T cells elicited by the CMV vector are restricted by Class II MHC or an ortholog thereof.

3. The method of claim 2, wherein at least 20% of the CD8+ T cells are restricted by Class II MHC or an ortholog thereof.

4. The method of claim 3, wherein fewer than 10% of the CD8+ T cells are restricted by MHC-E or an ortholog thereof.

5. The method of claim 2, wherein at least 30% of the CD8+ T cells are restricted by Class II MHC or an ortholog thereof.

6. The method of claim 2, wherein at least 40% of the CD8+ T cells are restricted by Class II MHC or an ortholog thereof.

7. The method of claim 2, wherein at least 50% of the CD8+ T cells are restricted by Class II MHC or an ortholog thereof.

8. The method of claim 2, wherein at least 60% of the CD8+ T cells are restricted by Class II MHC or an ortholog thereof.

9. The method of claim 2, wherein at least 75% of the CD8+ T cells are restricted by Class II MHC or an ortholog thereof.

10. The method of claim 1, wherein the subject has been previously exposed to CMV.

11. The method of claim 1, wherein the subject is a human or nonhuman primate.

12. The method of claim 1, wherein administering the CMV vector comprises subcutaneous, intravenous, intramuscular, intraperitoneal, or oral administration of the CMV vector.

13. The method of claim 1, wherein the first MRE of the CMV vector silences expression of IE2 or an ortholog thereof in the presence of miR-142-3p.

14. The method of claim 1, wherein the first MRE of the CMV vector silences expression of UL79 or an ortholog thereof in the presence of miR-142-3p.

15. The method of claim 1, wherein the CMV vector further comprises a second MRE operably linked to a CMV gene that is essential or augmenting for CMV growth, and wherein the second MRE silences expression in the presence of miR-142-3p.

16. The method of claim 15, wherein the first MRE of the CMV vector silences expression of IE2 or an ortholog thereof in the presence of miR-142-3p, and wherein the second MRE of the CMV vector silences expression of UL79 or an ortholog thereof in the presence of miR-142-3p.

17. The method of claim 1, wherein the at least one heterologous antigen comprises a pathogen-specific antigen, a tumor antigen, a tissue-specific antigen, or a host self-antigen.

18. The method of claim 17, wherein the pathogen specific antigen is derived from human immunodeficiency virus, simian immunodeficiency virus, herpes simplex virus, hepatitis B virus, hepatitis C virus, papillomavirus, *Plasmodium* parasites, or *Mycobacterium tuberculosis*.

19. The method of claim 17, wherein the tumor antigen is related to acute myelogenous leukemia, chronic myelogenous leukemia, myelodysplastic syndrome, acute lymphoblastic leukemia, chronic lymphoblastic leukemia, non-Hodgkin's lymphoma, multiple myeloma, malignant melanoma, breast cancer, lung cancer, ovarian cancer, prostate cancer, pancreatic cancer, colon cancer, renal cell carcinoma (RCC), or germ cell tumors.

20. The method of claim 1, wherein the CMV vector does not express an active UL79 protein or an ortholog thereof.

21. The method of claim 1, wherein the CMV vector does not express an active UL82 (pp71) protein or an ortholog thereof.

22. The method of claim 1, wherein the CMV vector does not express an active US11 protein or an ortholog thereof.

23. The method of claim 1, where the CMV vector (a) does not express an active UL79 protein or an ortholog thereof, (b) does not express an active UL82 (pp71) protein or an ortholog thereof, and (c) does not express an active US11 protein or an ortholog thereof.

* * * * *